(12) United States Patent
Kaddoura

(10) Patent No.: US 10,616,324 B1
(45) Date of Patent: Apr. 7, 2020

(54) DECENTRALIZED LEDGER SYSTEM AND METHOD FOR ENTERPRISES

(71) Applicant: Architecture Technology Corporation, Hopkins, MN (US)

(72) Inventor: Maher N Kaddoura, Maple Grove, MN (US)

(73) Assignee: ARCHITECTURE TECHNOLOGY CORPORATION, Minneapolis, MN (US)

( * ) Notice: Subject to any disclaimer, the term of this patent is extended or adjusted under 35 U.S.C. 154(b) by 80 days.

(21) Appl. No.: 15/654,960

(22) Filed: Jul. 20, 2017

(51) Int. Cl.
*H04L 29/08* (2006.01)
*H04L 12/26* (2006.01)

(52) U.S. Cl.
CPC .......... *H04L 67/1076* (2013.01); *H04L 43/04* (2013.01); *H04L 67/1078* (2013.01); *H04L 69/329* (2013.01)

(58) Field of Classification Search
CPC . H04L 67/1076; H04L 43/04; H04L 67/1078; H04L 69/329
USPC ........................................................ 709/223
See application file for complete search history.

(56) References Cited

U.S. PATENT DOCUMENTS

| | | | | |
|---|---|---|---|---|
| 7,792,915 B2* | 9/2010 | Berkey | ................ | H04L 67/104 709/209 |
| 9,722,790 B2* | 8/2017 | Ebrahimi | .............. | H04L 9/3066 |
| 9,973,341 B2* | 5/2018 | Ferrin | .................... | H04L 9/3247 |
| 10,097,356 B2* | 10/2018 | Zinder | .................. | H04L 9/3247 |
| 10,135,870 B2* | 11/2018 | Castinado | ............... | H04L 63/20 |
| 10,142,312 B2* | 11/2018 | Johnsrud | ................ | H04L 63/08 |
| 10,142,347 B2* | 11/2018 | Kurian | .................. | H04L 63/102 |
| 2016/0342977 A1* | 11/2016 | Lam | ........................ | G06Q 20/02 |
| 2017/0046664 A1* | 2/2017 | Haldenby | .............. | G06Q 50/18 |
| 2017/0116693 A1* | 4/2017 | Rae | ..................... | G06Q 20/3827 |
| 2017/0132630 A1* | 5/2017 | Castinado | .......... | G06Q 20/4014 |
| 2017/0213287 A1* | 7/2017 | Bruno | ..................... | G06Q 40/04 |
| 2017/0289111 A1* | 10/2017 | Voell | .................... | H04L 63/0435 |
| 2017/0316390 A1* | 11/2017 | Smith | .................. | G06Q 20/407 |
| 2017/0317997 A1* | 11/2017 | Smith | .................... | H04L 9/0891 |
| 2017/0337534 A1* | 11/2017 | Goeringer | ............. | H04L 9/3239 |
| 2017/0352027 A1* | 12/2017 | Zhang | .................... | H04L 9/0825 |
| 2018/0019867 A1* | 1/2018 | Davis | .................... | H04L 9/0637 |
| 2018/0025435 A1* | 1/2018 | Karame | ................ | G06Q 40/12 705/30 |
| 2018/0032383 A1* | 2/2018 | Surcouf | .................... | G06F 9/546 |
| 2018/0039667 A1* | 2/2018 | Pierce | ............... | G06F 17/30371 |
| 2018/0219669 A1* | 8/2018 | Chen | ........................ | H04L 9/002 |
| 2018/0285217 A1* | 10/2018 | Smith | ................. | G06F 11/1489 |
| 2018/0294955 A1* | 10/2018 | Rhie | ..................... | H04L 9/0637 |

* cited by examiner

*Primary Examiner* — Vivek Srivastava
*Assistant Examiner* — Binod J Kunwar

(57) ABSTRACT

A computer-implemented method for managing enterprise transactions includes creating an overlay to a physical communications network, adding one or more nodes to the overlay, designating one or more nodes of the overlay as super nodes, generating a distributed ledger to store the transactions, and replicating the distributed ledger to all nodes of the overlay. Generating the distributed ledger includes receiving, at the super nodes, transactions from the one or more nodes, assigning, by the super nodes, the transactions to a variable size block, validating, by the super nodes, the variable size block, and linking the validated variable size block to the distributed ledger.

16 Claims, 24 Drawing Sheets

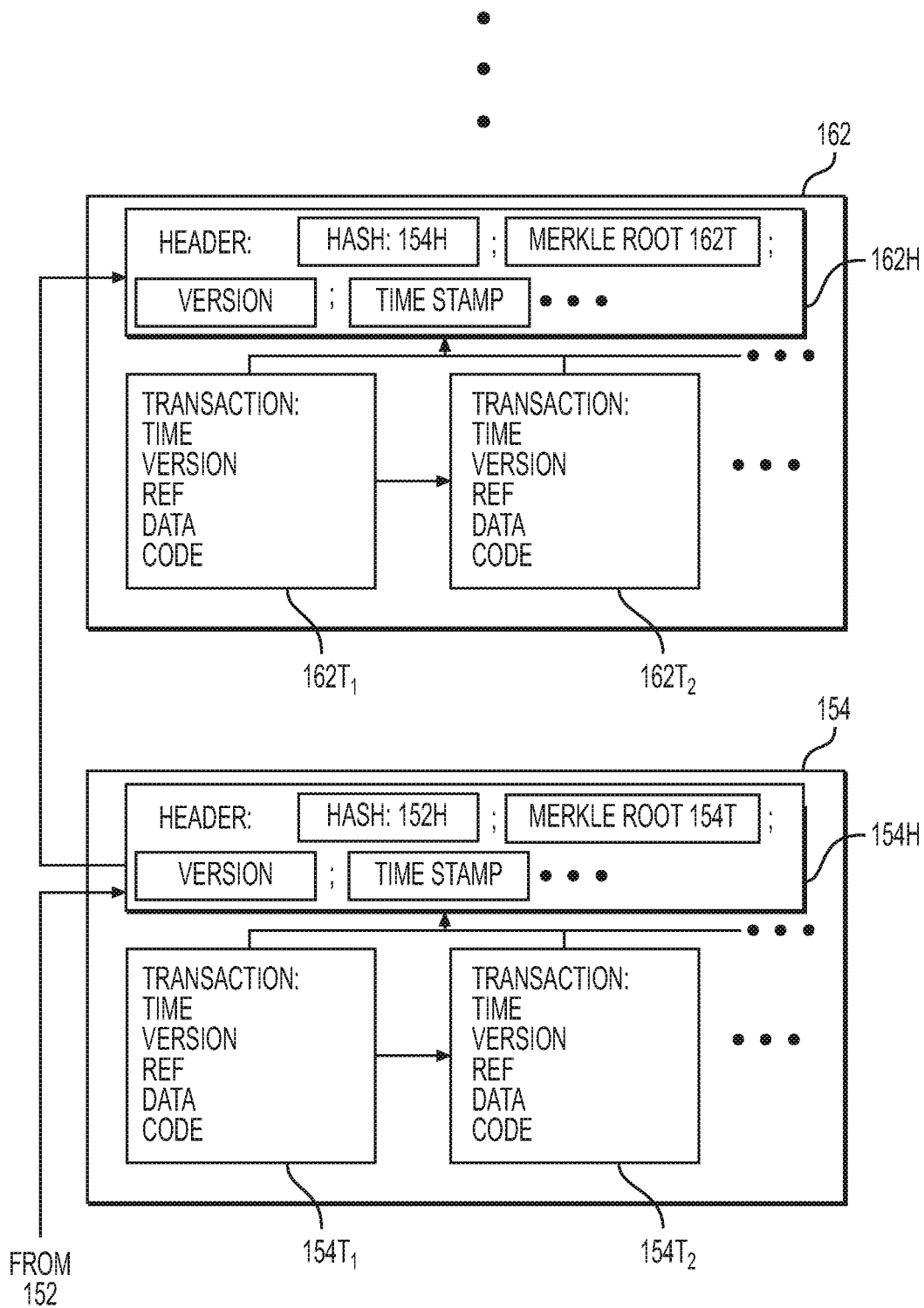
FIG. 1E(1)

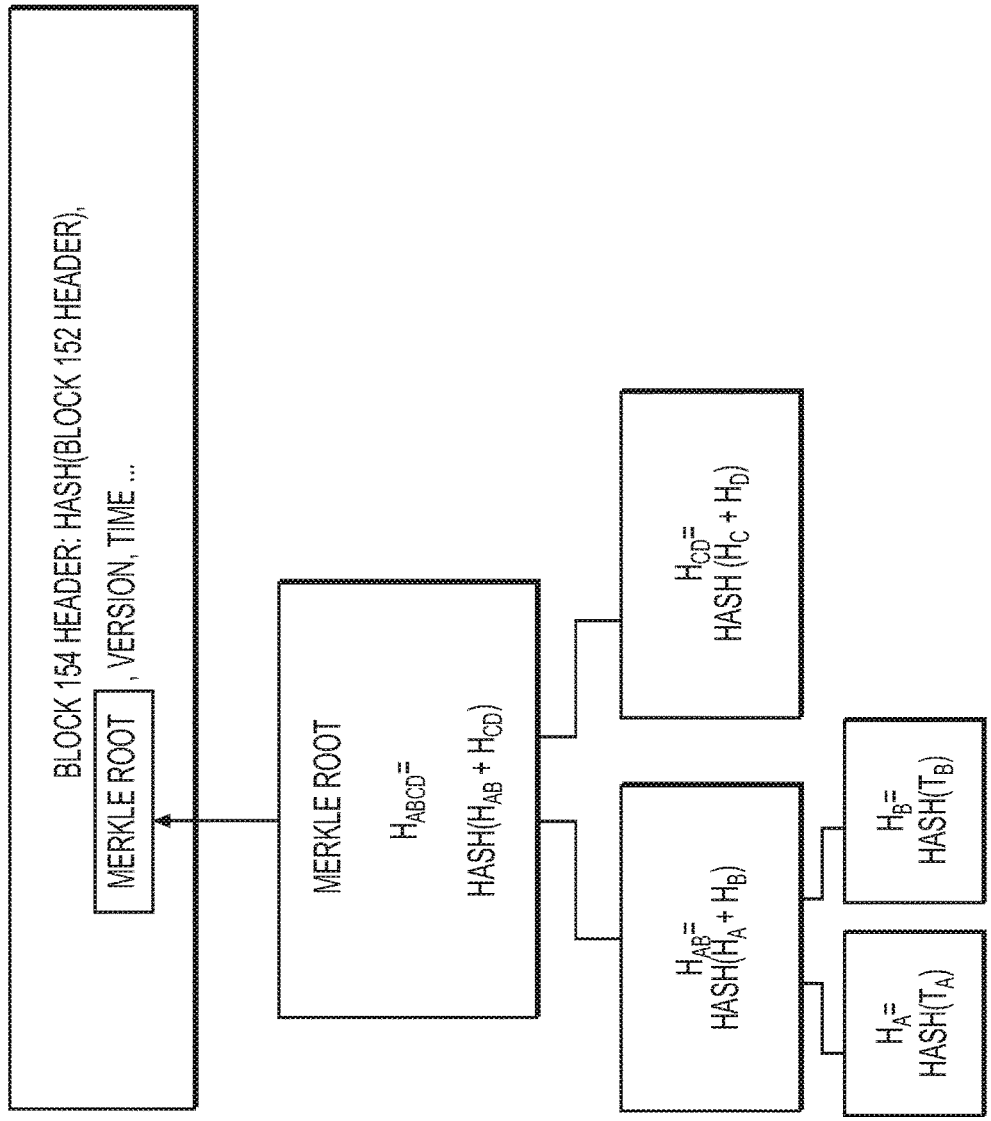
FIG. 1E(2)

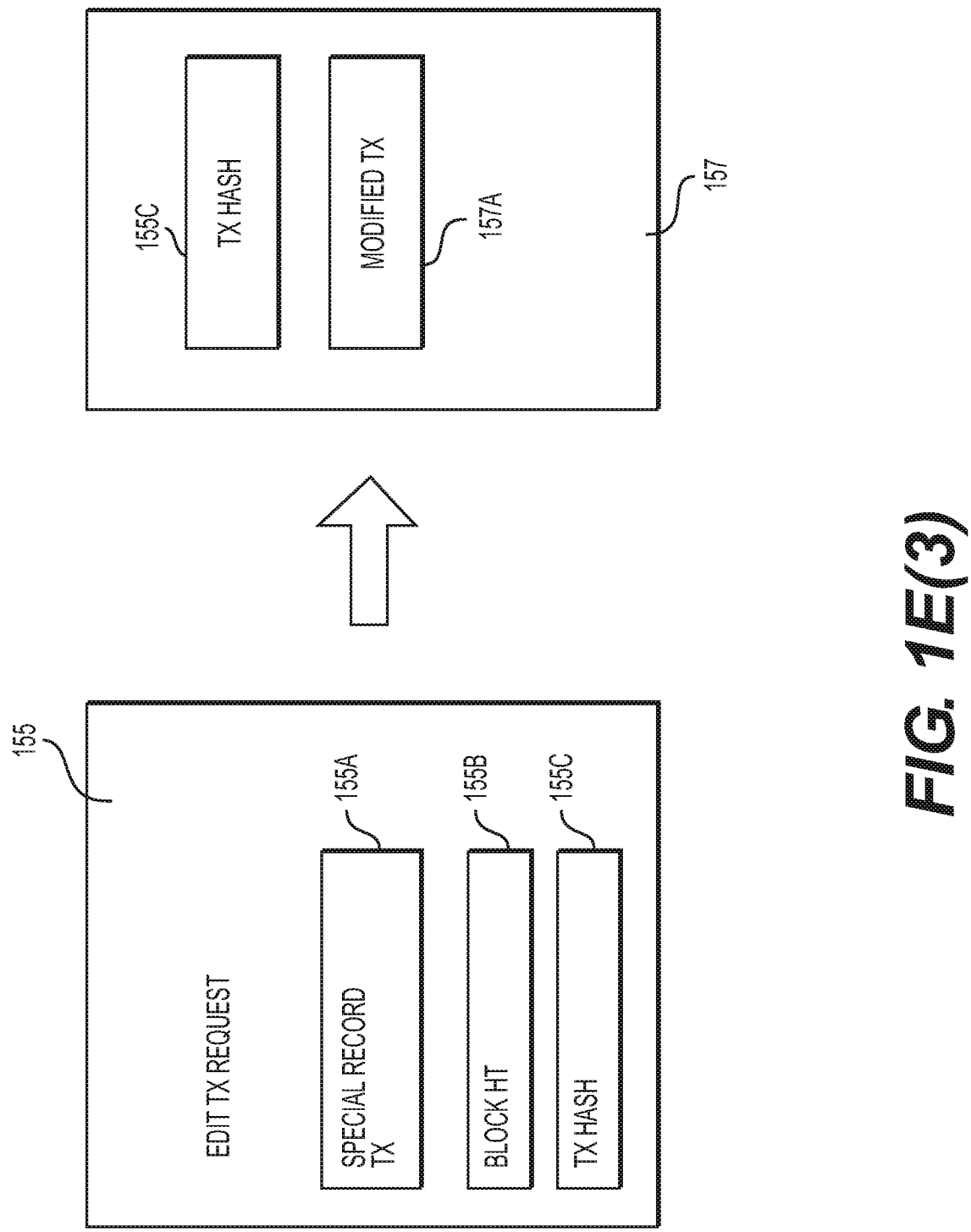
FIG. 1E(3)

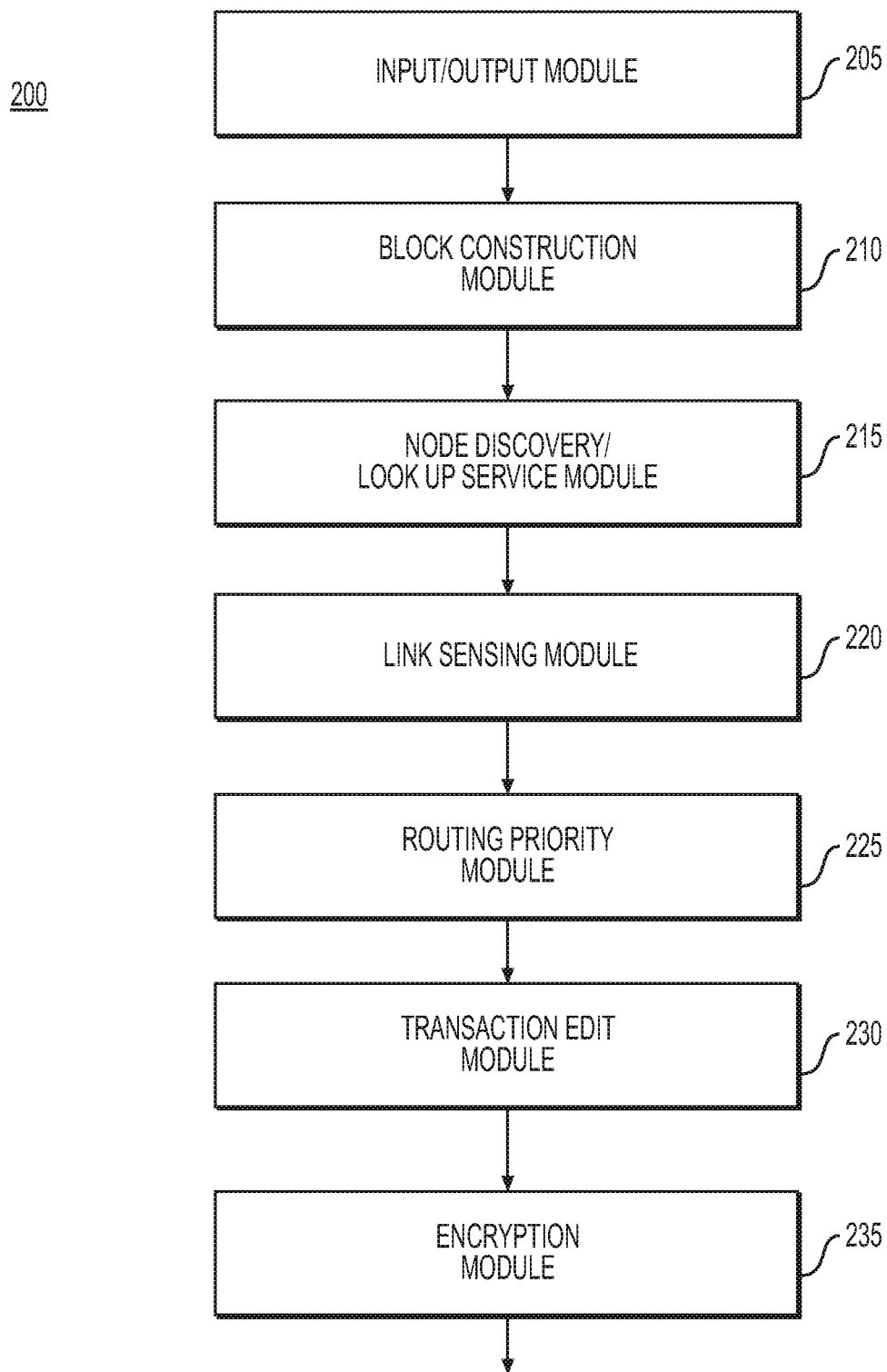
*FIG. 2B(1)*

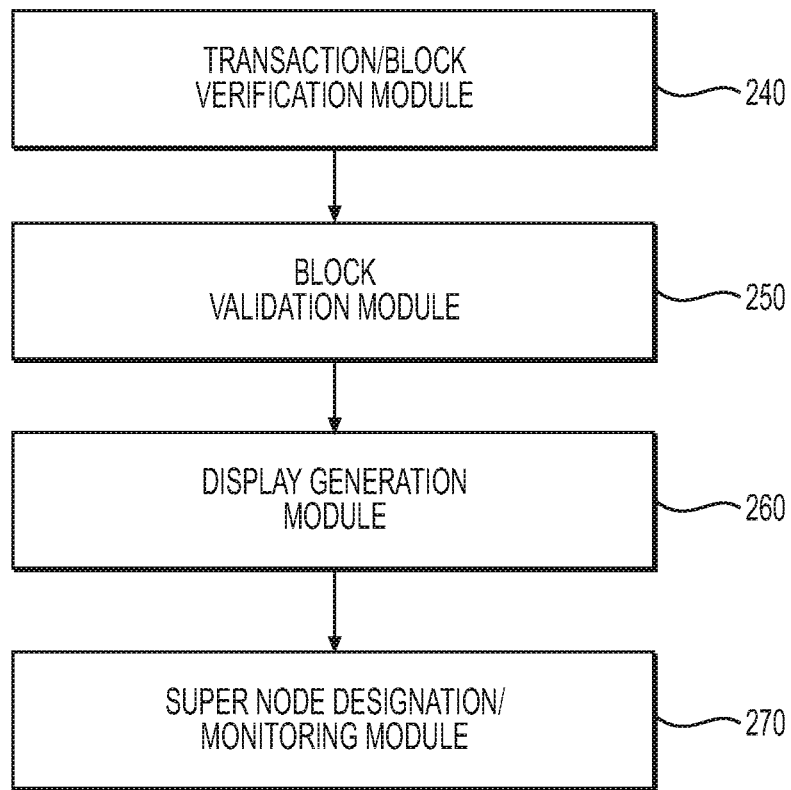
FIG. 2B(2)

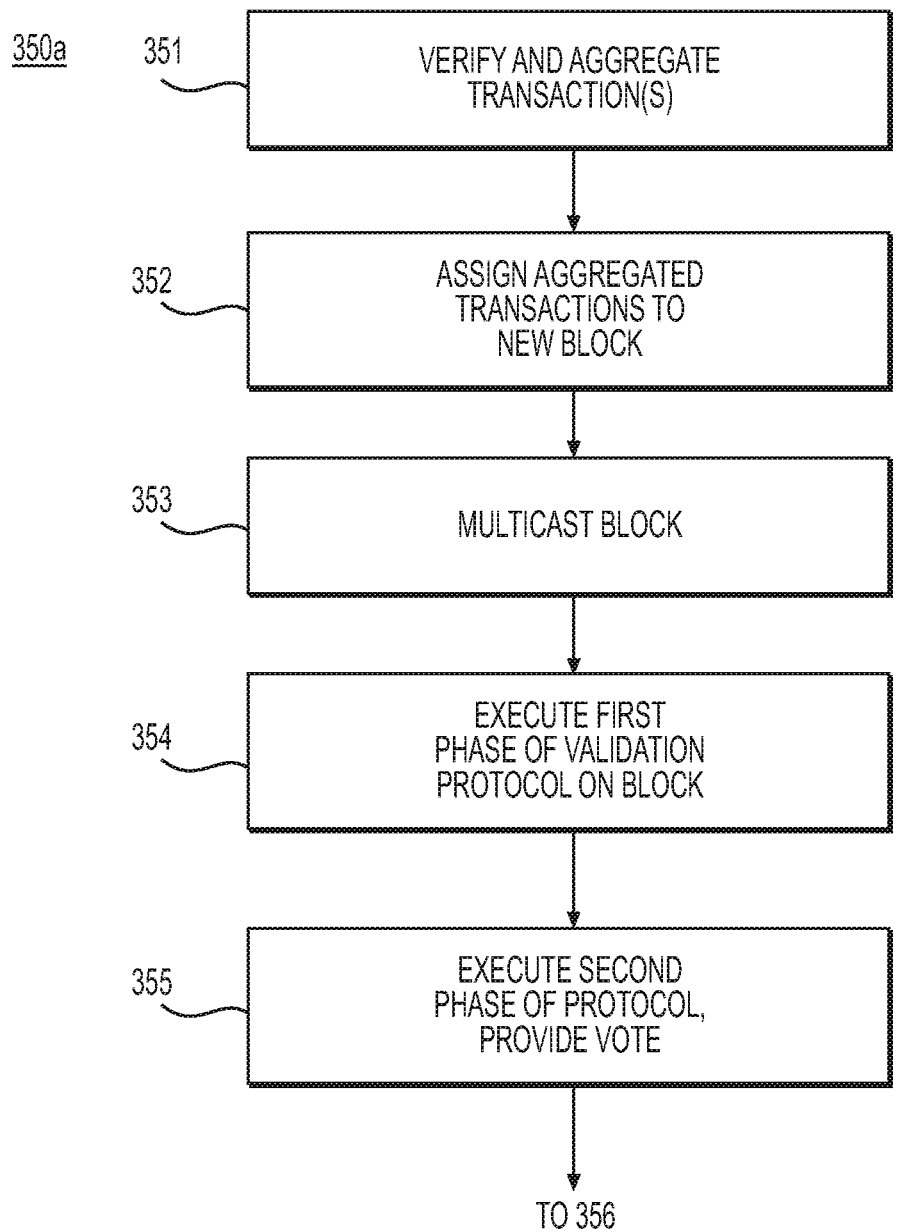
FIG. 3F(1)

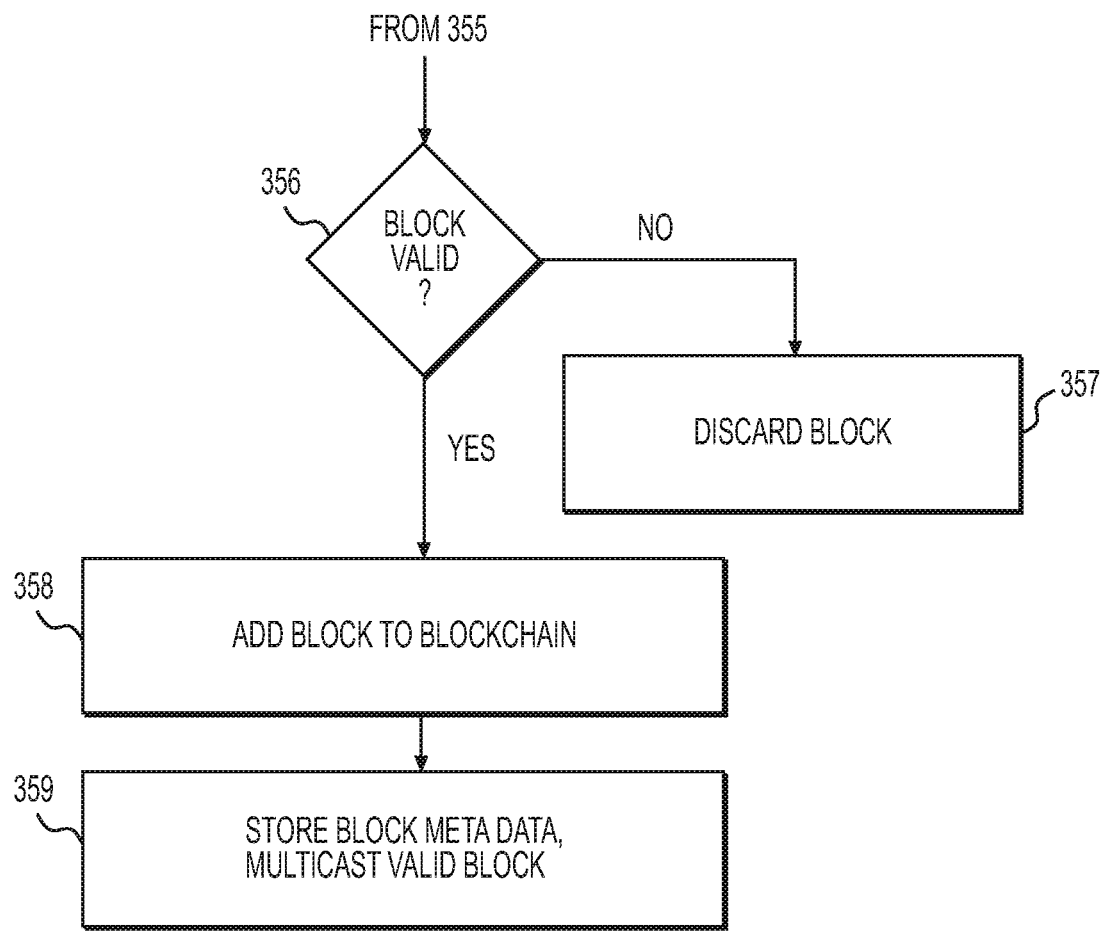
FIG. 3F(2)

DECENTRALIZED LEDGER SYSTEM AND METHOD FOR ENTERPRISES

BACKGROUND

Current centralized architecture information systems are expensive to build and maintain, and may be inefficient and vulnerable to cyber-attack. An information system that employs a decentralized ledger may overcome some of the above-noted limitations inherent in a centralized architecture messaging system, but such a decentralized architecture system may require large bandwidth capacity and large computational resources to exchange information among system users.

A blockchain is a distributed database that may be used to maintain a continuously growing list of records, sometimes called blocks. Each block contains a timestamp and a link to a previous block. Each block may contain one or more transactions and a block header. A blockchain typically is managed by peer-to-peer nodes in a network, the nodes collectively adhering to a protocol for validating new blocks. By design, blockchains are inherently resistant to modification of the data. Typically, once recorded, the data in any given block cannot be altered retroactively without the alteration of all subsequent blocks and the collusion of the network. Functionally, therefore, a blockchain may serve as "an open, distributed ledger" that records transactions in a verifiable and permanent way without use of a trusted authority or central server. This makes blockchains potentially suitable for recording events and other records management activities, identity management, transaction processing, and documenting provenance.

One feature of blockchains, which is both an advantage and a disadvantage, is immutability. Blockchains typically are "append-only" systems, meaning data may be added to a blockchain, but cannot be taken away or modified. The limited ability to modify or delete data resident in a blockchain may prevent use of this technology in some applications.

An emerging technology that may be incorporated into blockchains is known as "smart contracts." Smart contracts are essentially a sequence of computer instructions, residing on the blockchain, that automatically execute according to those instructions when specified events occur. However, because blockchains largely are immutable, should the computer instructions contain an error, the only way to update the smart contract may be to post a new smart contract to the blockchain. The new smart contract then applies to subsequent blocks, but may not affect previous blocks. The new smart contract also may force a "hard fork" in the blockchain, thereby complicating reconstruction of subsequent blocks.

Consensus is a method for validating the order of blocks and their transactions, on a blockchain. The correct ordering of transactions may be important, because many transactions have a dependency on one or more prior transactions. On a blockchain, no centralized authority determines the transaction order; instead, many validating nodes (or peers) implement the consensus protocol. Consensus ensures that a quorum of nodes agree on the order in which transactions are appended to the blockchain. By resolving any discrepancies in the proposed transaction order, consensus guarantees that all blockchain nodes are operating on an identical ledger. In other words, consensus guarantees the integrity and consistency of all blockchain transactions.

SUMMARY

A computer-implemented method for managing enterprise transactions includes creating an overlay to a physical communications network, adding one or more nodes to the overlay, designating one or more nodes of the overlay as super nodes, generating a distributed ledger to store the transactions, and replicating the distributed ledger to all nodes of the overlay. Generating the distributed ledger includes receiving, at the super nodes, transactions from the one or more nodes, assigning, by the super nodes, the transactions to a variable size block, validating, by the super nodes, the variable size block, and linking the validated variable size block to the distributed ledger.

A computer-implemented method for storing and managing enterprise data using a distributed ledger includes receiving by a processor, transactions from nodes in a communications network; through an application layer of the communications network, aggregating one or more of the transactions in a block, comprising verifying each of the one or more transactions, creating a hash of the one or more transactions, and adding the one or more transaction to a block and adding the hash to a header of the block; through the application layer, validating the block, comprising: executing a consensus algorithm by a plurality of trusted nodes in the communications network, and generating a hash of the block; linking the block to a predecessor block in the distributed ledger, comprising verifying the hash of the block is lower than a hash of a top block in the distributed ledger; and replicating the distributed ledger across the communications network, comprising multicasting the block to each node in the communications network.

A non-transitory, computer-readable storage medium having encoded thereon a program comprising machine instructions implementing a distributed ledger to store and manage enterprise transactions, wherein one or more processors execute the machine instructions to create an overlay to a physical communications network, comprising the processors: identifying physical nodes in the physical communications network, assigning an overlay node to a physical node, connecting the overlay node to the physical node through an application layer of the physical communications network; designate one or more overlay nodes of the overlay as super nodes; receive, at physical nodes corresponding to the super nodes, transactions from physical nodes corresponding to the one or more overlay nodes; assign, through the super nodes, the transactions to a variable size block; validate, through the super nodes, the variable size block; link the validated variable size block to the distributed ledger; and replicate the distributed ledger at all overlay nodes of the overlay.

DESCRIPTION OF THE DRAWINGS

The detailed description refers to the following figures in which like numerals refer to like objects, and in which:

FIGS. 1E(1)-1E(3) illustrate aspects of blocks and transactions in the blockchain of FIG. 1D;

FIGS. 2B(1) and 2B(2) illustrate components of the example FREE system of FIG. 2A;

FIGS. 3A-3I illustrate example operations of the FREE system of FIGS. 2A-2B(2)

DETAILED DESCRIPTION

Figure 1A:
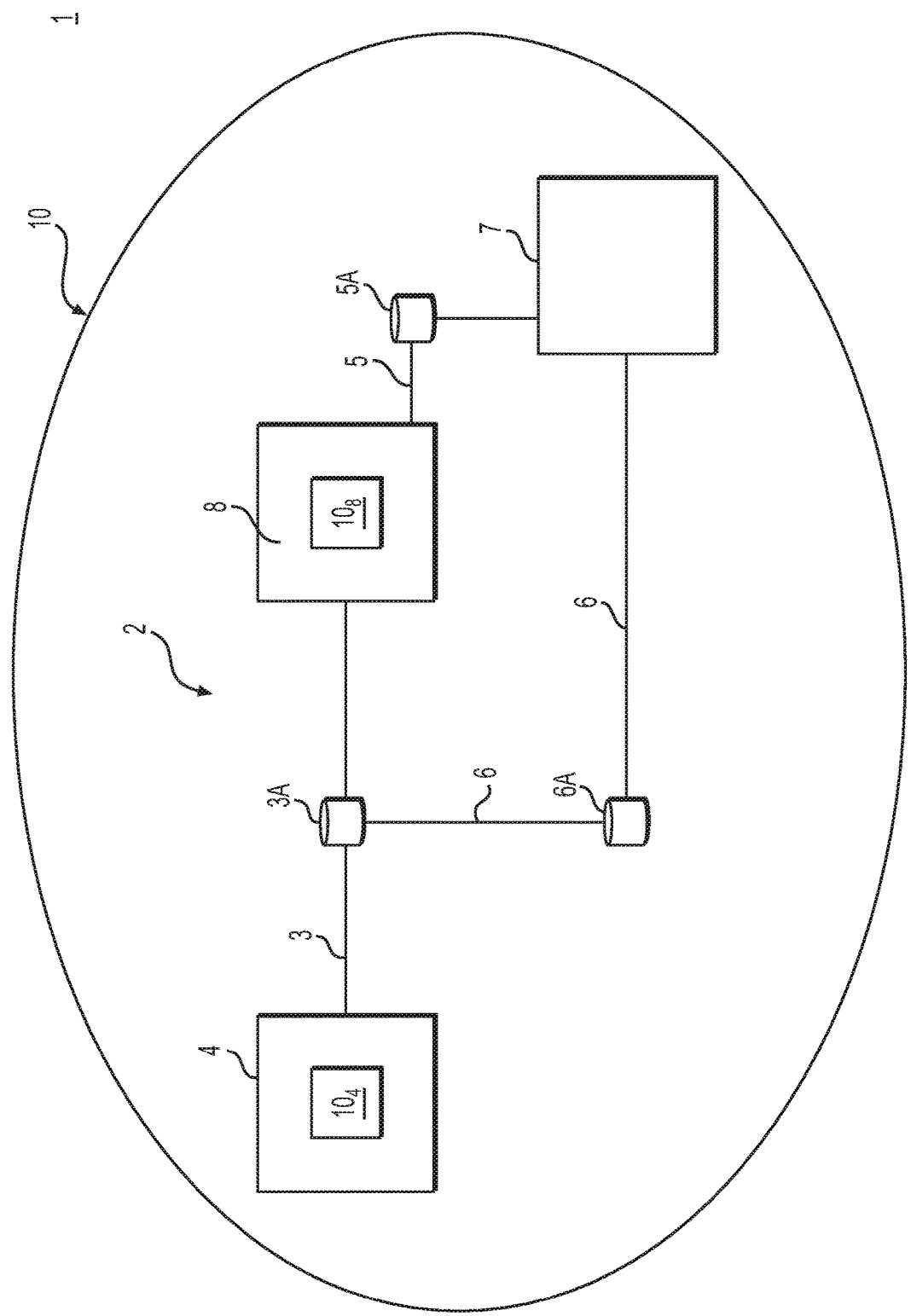
FIG. 1A illustrates an example environment in which a blockchain system for enterprise environments (FREE system) is implemented.

Information systems that are based on centralized architectures are expensive to build and maintain, and may be inefficient and vulnerable to cyber-attack. An information system that employs a decentralized ledger may be less expensive to implement, more efficient, and less prone to cyber-attack than a centralized architecture system. However, decentralized ledger systems may require large bandwidth capacity and large computational resources for efficient information exchange. In addition, some decentralized ledger system may impose delays in information exchange among system users. An example of such a decentralized ledger information system employs blockchain technology. A blockchain data structure is an ordered, back-linked list of blocks of transactions. The blockchain can be stored as a flat file or in a simple database. Blocks are linked back, each referring to the previous block in the chain. The "height" of a block in blockchain parlance refers to a distance from a first block to the block of interest. Each block within the blockchain is identified by a hash, typically generated using a cryptographic hash algorithm on the block header. Each block also references the previous block through a previous block hash field in the block header. The sequence of hashes linking each block to its predecessor creates a chain going back to the first block (a "genesis block") in the blockchain. The previous block hash field is inside the current block's block header and thereby affects the current block's hash. If the previous block is modified in any way, the previous block's hash may change. This necessitates a change in the previous block hash of the current block, which results in a change in the current block's hash. This effect ripples up through the blockchain. This cascading effect ensures that once a block has many subsequent blocks, that block cannot be changed without forcing a recalculation of all subsequent blocks. Because such a recalculation would impose an enormous computational load, the existence of a long chain of block makes the blockchain's "ancient history" immutable, which, in some applications is desirable to ensure transaction security.

Structurally, a block may be thought of as a container that aggregates one or more transactions for inclusion in the decentralized ledger. A block typically includes a header, which contains metadata followed by perhaps hundreds of transactions. The block header may include, in addition to the previous block hash, a timestamp. In some implementations, the block header may include a Merkle root, which is a hash of all transactions in the block. In some implementations, the block header also may include data structures that relate to a process for validating the block. The block header does not typically include the block's own hash. Instead, the block's hash is computed by each node in the blockchain network as the block is received from the network. The block hash may be stored in a separate database table as part of the block's metadata to facilitate indexing and faster retrieval of blocks from storage. The block's own hash is the primary data structure for identifying the block.

Some current blockchain implementations of decentralized ledger systems, such as Bitcoin, are Internet-based applications. Such decentralized ledger systems may be built on the assumptions that support for identity protection is needed; real-time exchange of information is not essential; a large pool of computing nodes is available for mining (validating) blocks; and sufficient bandwidth is available for transmission of information. Members (or conforming nodes) of a decentralized ledger are connected to each other in a best-effort fashion; a new member (node) discovers the network using, for example, domain name server (DNS) services or hardcoded addresses. Thus, the system is formed in an ad-hoc fashion, which results in a slow distribution of the records and slow blockchain buildup. These features may be acceptable in commercial environments, where large Internet resources are used to build and maintain decentralized ledgers. In addition, current blockchain implementations may apply to a network composed of a wide range of network topologies. However, as a result of these features, current blockchain designs may not be suitable for environments in which bandwidth and computation resources are limited, and where real-time or near real-time information exchange is desired or required.

Examples of blockchain implementations include digital-currency-based transaction systems (e.g., Bitcoin) and smart contracts systems. The limitations inherent in current blockchain designs do not adversely affect operation of these systems. A specific example of an information system is a messaging system. Messaging systems typically employ a centralized architecture and hence suffer from all the drawbacks of such a centralized architecture. Current blockchain designs could adversely affect operation of such a messaging system or an information system.

To overcome limitations inherent in both centralized ledger architecture systems and blockchain-based systems, disclosed herein is an efficient distributed ledger system for enterprise environments (FREE system), and corresponding method (FREE method). The FREE system and method improve on current distributed ledger technology to provide secure and efficient messaging and data transmission in specific environments as disclosed herein, including, for example, bandwidth-limited situations and environments. In an embodiment, the FREE system implements a distributed ledger using a permissioning system. Use of a permissioning system provides safe and secure message and data transmissions when an enterprise wants or needs control of transactions. In another embodiment, the FREE system implements a distributed ledger using a blockchain architecture. In one aspect of a blockchain implementation, the blockchain is an open blockchain. In another aspect, the blockchain is a permissioned blockchain. In an aspect of either blockchain implementation, the blockchain may be immutable. In another aspect of either blockchain implementation, the blockchain may be editable. Use of a permissioned blockchain allows the FREE system to exert more control over the generation and management of the blockchain with little effect on the security and efficiency of the blockchain as a decentralized or distributed ledger. Aspects of the open and permissioned blockchain embodiments are disclosed in more detail with respect, inter-alia, to FIGS. 1E(1)-1E(3). In embodiments, the FREE system may embed network protocols and quality of service (QoS) techniques into a blockchain to increase its efficiency. The FREE system may be implemented at the application level to overcome network constraints such as firewalls and crypto-partitioned networks. The FREE system may take the form of a standalone product that can operate efficiently in any enterprise network. In an embodiment, the FREE system may include an overlay multicast protocol to optimize the flow of records in an underlying network to which the FREE system is an overlay. This embodiment of the FREE system further may include a lookup service that enables members of or on an underlying physical network to "discover each other," an efficient link sensing mechanism, and a block validation protocol. In an aspect of the embodiment, the block validation protocol may be implemented on application specific integrated circuits (ASICs). In another aspect, the block validation protocol may be executed by a CPU. In an aspect of the embodiment, the FREE system may employ stream-based ciphers and identity-based encryption, a mechanism for editing and storing records using a smart contract approach, and hardware devices to provide additional security.

The disclosure that follows may refer generally to the following terms, and in some disclosed embodiments, adopts the definitions provided for these terms:

A consensus mechanism is an algorithm or program used by network validators (nodes) and through which a majority of (or in some cases all) network validators come to agreement on the state of a distributed ledger. The mechanism may include a set of rules and procedures that allows maintaining a coherent set of facts among or between multiple participating nodes. In some blockchain implementations, the "longest chain" of the blockchain is considered the valid distributed ledger.

A crypto system may be used by a network to secure transactions in a verifiable database that cannot be changed without being noticed.

A distributed ledger system is a network that typically utilizes cryptographic technology to verify or store votes (e.g., hashes) from certain network nodes.

An on-chain transaction is one with which users (nodes) settle transactions on the public blockchain. For instance, in the first couple years of its existence, Bitcoin users sent bitcoins to one another directly through the blockchain because there were no external intermediaries or custodians available.

Off-chain applies to exchanges that exist to provide off-chain services that are managed by internal accounting records (e.g. exchanges perform buy/sell operations off the chain via their own private database).

A permissioned system is one in which the identity for users (nodes) is whitelisted (or blacklisted) through a "know your customer" (KYC) procedure.

A permissionless system is one in which the identity of participants is either pseudo-anonymous or anonymous. Many blockchain implementations are permissionless.

A smart contract is a rules engine including cryptographically assured logic that may execute on the occurrence of specified events.

As noted above, blockchain architectures may be implemented with certain limiting assumptions such as speed of block buildup (the Bitcoin blockchain application limits block addition to a maximum of one block every ten minutes), and a large computing capability in the network (i.e., the Internet), which are acceptable is many environments (e.g., commercial environments) where large Internet resources are used to build and maintain decentralized ledgers. However, in other environments, network resources may be limited, and some network nodes may have connectivity only through tactical links (typically used only by military organizations) or may operate in areas in which active and passive measures are being taken to deny access by the nodes. In these environments, the FREE system may use efficient communications networking protocol embodiments that allow nodes to discover available network resources.

The FREE system may deploy a network overlay with a multicast protocol, which is executed through the application layer of the underlying physical network, to connect nodes in the overlay network. The FREE system may include mechanisms to periodically adjust the network overlay topology based on the location of the nodes and available resources in the underlying physical network. The FREE system may incorporate quality of service (QoS) capabilities including priority-based routing by which messages and transactions may be assigned priorities. In an embodiment, the FREE system may include a lookup service that enables the nodes in the overlay network to dynamically discover each other, and link sensing by which the FREE system may monitor available bandwidth in the underlying physical network between nodes. In addition, the FREE system may deploy queueing mechanisms to allocate bandwidth to records (messages and transactions) based on their priorities, and to shape traffic over links.

Figure 2A:
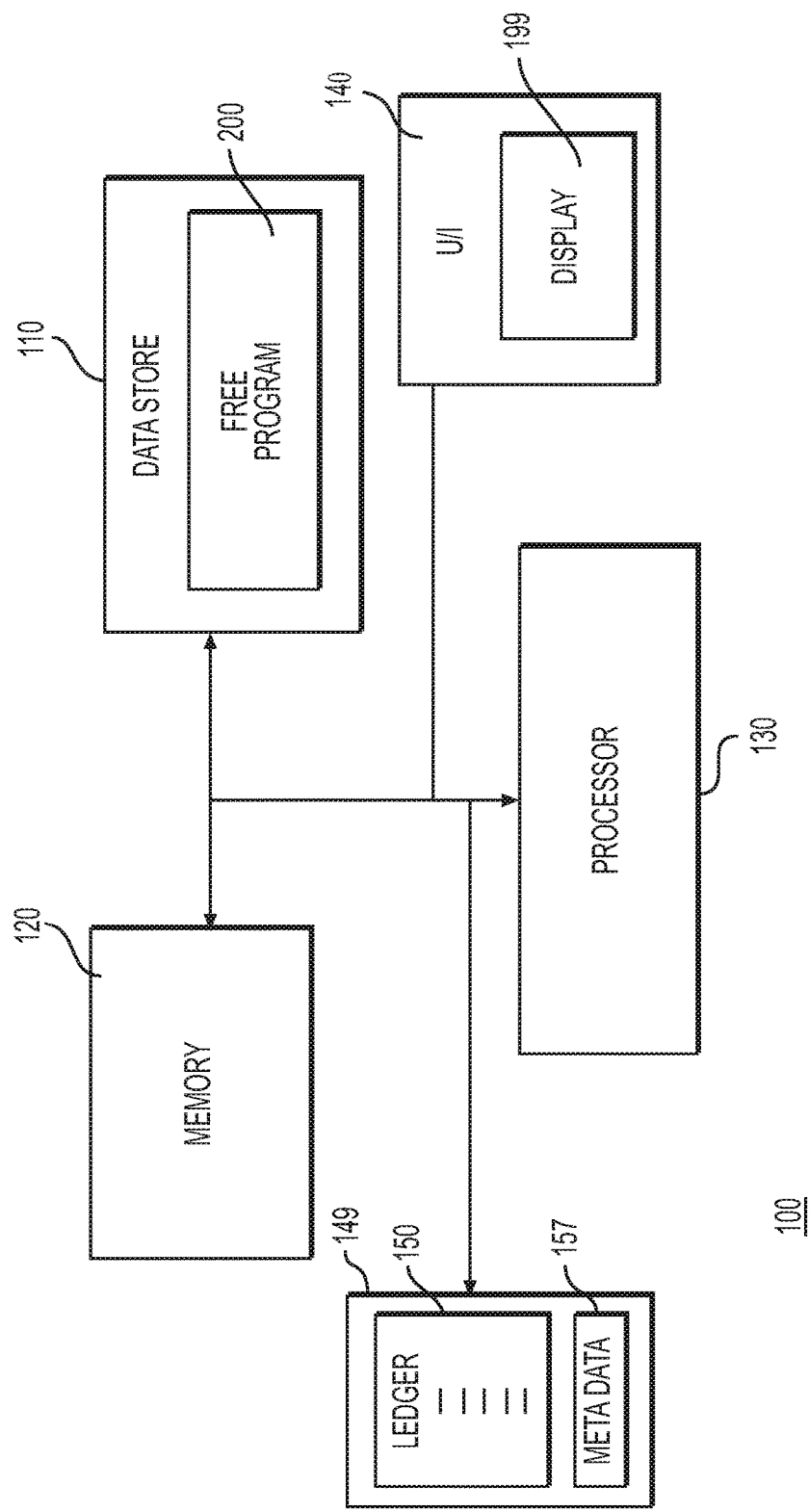
FIG. 2A illustrates an example FREE system.

FIG. 1A illustrates an example environment in which a decentralized ledger system for enterprises (e.g., the FREE system) may be implemented. In FIG. 1A, environment 1 includes physical network 2 shown including nodes 4 and 8 connected through link 3, and node 7 connected to node 8 through link 5. Link 3 may include network component 3A, which may be a network switch or router; link 5 may similarly include network component 5A. In addition, nodes 4 and 7 may communicate directly without going through node 8, using link 6 between routers 3A and 6A. The network 2 may be a wide area network (WAN) such as the Internet, a local area network (LAN), a wired or wireless communications network, a cellular communications network, a virtual private network, or similar networks in which information (records, messages, transactions, data) are communicated between the nodes 4 and 8. The network 2 may be a centralized or a decentralized ledger system. The physical network 2 may include multiple topologies; for example, the physical network 2 may include multiple communications modes, including wireline and wireless, cellular and satellite. However, for purposes of illustration, network 2 is a wireless wide area network (e.g., the Internet). Also shown in FIG. 1A is network overlay 10, which may be generated by operation of the decentralized ledger system for an enterprise (FREE system 100—see FIG. 2A), and which uses aspects of the communications infrastructure of network 2 in a distributed manner. In an example implementation of the FREE system 100, some or all nodes in the network 2 may include components of the FREE system 100; the components are illustrated in FIG. 1A as components $10_4$ and $10_8$. As a further example, node 4 may be associated with a fixed computer. The computer may include elements of the FREE system 100; specifically, the computer associated with node 4 may include, as component $10_4$, in a computer-readable storage medium, some or all the modules of FREE program 200, an example of which is shown in FIGS. 2B(1)-2B(2).

While the physical network 2 may take the form of a client-server network or a peer-to-peer network, the corresponding network overlay 10 may take the form of a hybrid between a true peer-to-peer network and a client-server network. With either architecture, the nodes in the network overlay 10 may correspond to a subset of the nodes in the physical network 2, and data still are exchanged directly over the underlying physical (e.g., TCP/IP) network 2. However, the application layer of the physical network 2 standardizes communication, and the nodes of the network overlay 10 are able use the application layer of the physical network 2 to communicate with each other directly using, for example, the Open Systems Interconnection (OSI) Model, Layer 7 (application Layer), which supports application and end-user processes. Communications resources are identified, quality of service is identified, user authentication and privacy are considered, and any constraints on data syntax are identified. Everything at this layer is application-specific. The application layer provides services for file transfers, e-mail, and other network software services. For example, file transport protocol (FTP) is an application that exists entirely in the application level. When identifying communications resources, the application layer determines the identity and availability of communication resources for an application with data to transmit. When determining resource availability, the application layer decides whether sufficient network resources for the requested communication are available. Thus, the network overlay 10 is used for indexing and node discovery, making the network overlay independent from the topology of the physical network 2.

The FREE system 100 (FIG. 2A) may be applicable to enterprises with undefined boundaries and rapidly changing members and to enterprises having defined boundaries and stable membership. The FREE system 100 may be used in certain permanent facilities such as embassies, government facilities, prisons, military installations, stadiums and arenas, hospitals, public transportation facilities, and landmarks, and in temporary applications including disaster recovery operations, emergency operations, and homeland security operations. The FREE system 100 may be used in any situation or at any enterprise, facility, or locale to establish a controlled environment (a hybrid network overlay) in which certain entities can access a decentralized ledger used to ensure communications integrity.

Figure 1B:
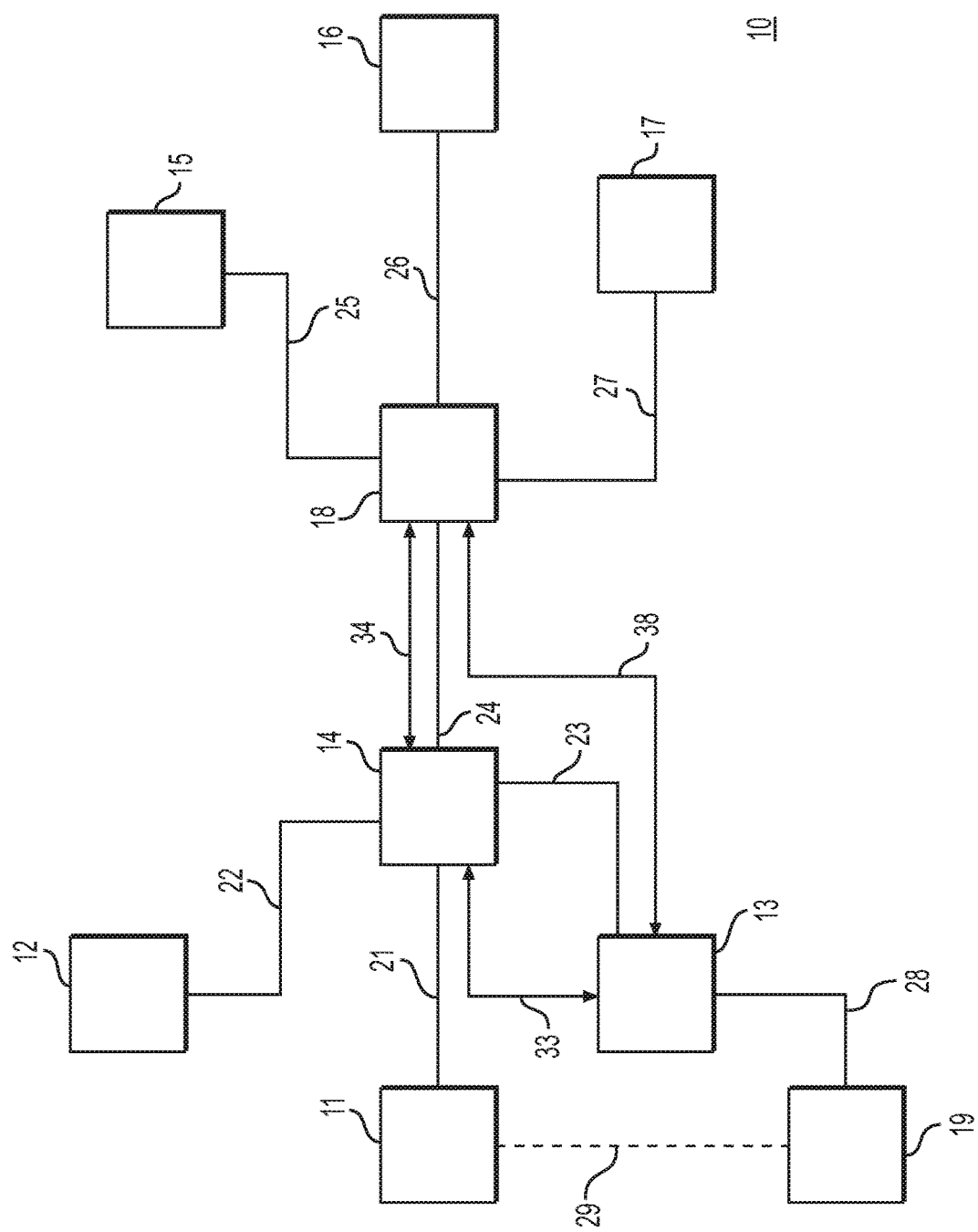
FIG. 1B illustrates example aspects of the FREE system including a network overlay.

FIG. 1B illustrates an example of a hybrid network overlay implemented through a FREE system embodiment. In FIG. 1B, network overlay 10 includes mobile nodes 11, 12, and 14-17, and fixed node 13. Once accepted (the process for which may include a KYC mechanism or other mechanisms, as disclosed herein) into the network overlay 10, a node may be referred to as a "conforming node." The network overlay 10 also includes fixed central node 18, in which components of FREE system 100 (FIG. 2A) may be installed. Additional fixed or mobile nodes may be added over time, and nodes also may be deleted, Components of the FREE system 100 are installed at each of the nodes 11-17. The nodes 14-17 connect to the central node 18 through links 24-27; the nodes 11-13 connect to node 14 through links 21-23. The nodes 11-17 may consist of computing devices. Some computing devices may be automated or autonomous. Other computing devices may function when operated by a human user. Some computing devices may include both autonomous operations and human user operations. The computing devices may include smart phones and various other communications devices, and laptop or fixed computers, for example. The nodes and their computing devices may have Internet Protocol addresses or MAC addresses through which the computing devices are addressed and recognized in the network 2. The nodes 11-17 and their associated computing devices may be registered with or a part of an existing enterprise. The enterprise may be a military or non-military government agency, a law enforcement agency, or a commercial entity. The enterprise may be a permanent enterprise or an ad hoc, temporary enterprise. The enterprise may adopt the FREE system 100 to generate the network overlay 10 in order to improve records handling among members of the enterprise. For example, the enterprise may use the network overlay 10 to provide rapid, secure email messaging and data exchange among enterprise members in bandwidth-limited conditions. Other nodes may seek to join the network overlay 10. A node may seek to join the network overlay 10 by, for example, sensing the network overlay 10, or because of addition of the node's computing device to the enterprise. Mobile nodes may be instantiated on a manned aircraft, a UAV/UAS, a manned aircraft, a tethered balloon, a motor vehicle, a train, and a ship. Fixed nodes may exist as or at a temporary structure or a permanent structure such as a building. In FIG. 1B, mobile nodes 11 and 12 are seen to be linked to mobile node 14. For purposes of illustration only, the nodes 11-18 may be associated with a wildfire fighting organization, with nodes 11 and 12 instantiated on respective UAVs controlled by devices mounted on a mobile unit (e.g., a truck) at node 14. Node 13 may be instantiated at a fixed location (e.g., a local control center) and node 18 may be instantiated at a permanent control center (e.g., a building). Nodes 15-17 may be associated with mobile firefighting units (e.g., the nodes may be associated with mobile devices used by individual firefighters). Node 19 may be associated with an additional firefighting asset brought in to combat the wildfire. In this illustrative example, some or all devices associated at the nodes 11, 12, and 14-17 may be known (e.g., the device IDs may be registered with the local control center at node 13 and/or the permanent control center at node 18).

Figure 1C:
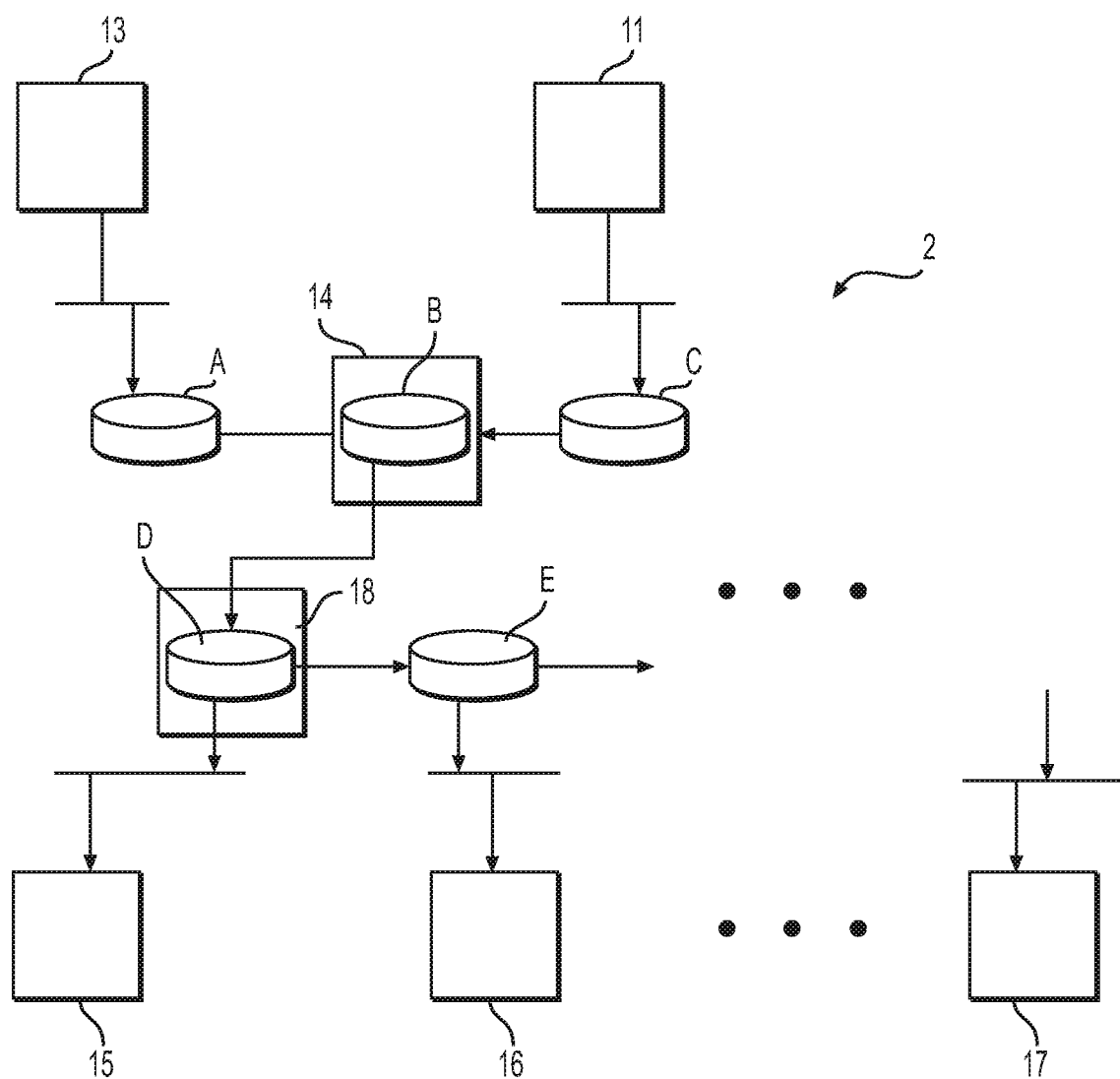
FIG. 1C illustrates a hybrid source/shared tree for routing messages in the network overlay of FIG. 1B.
Figure 1D:
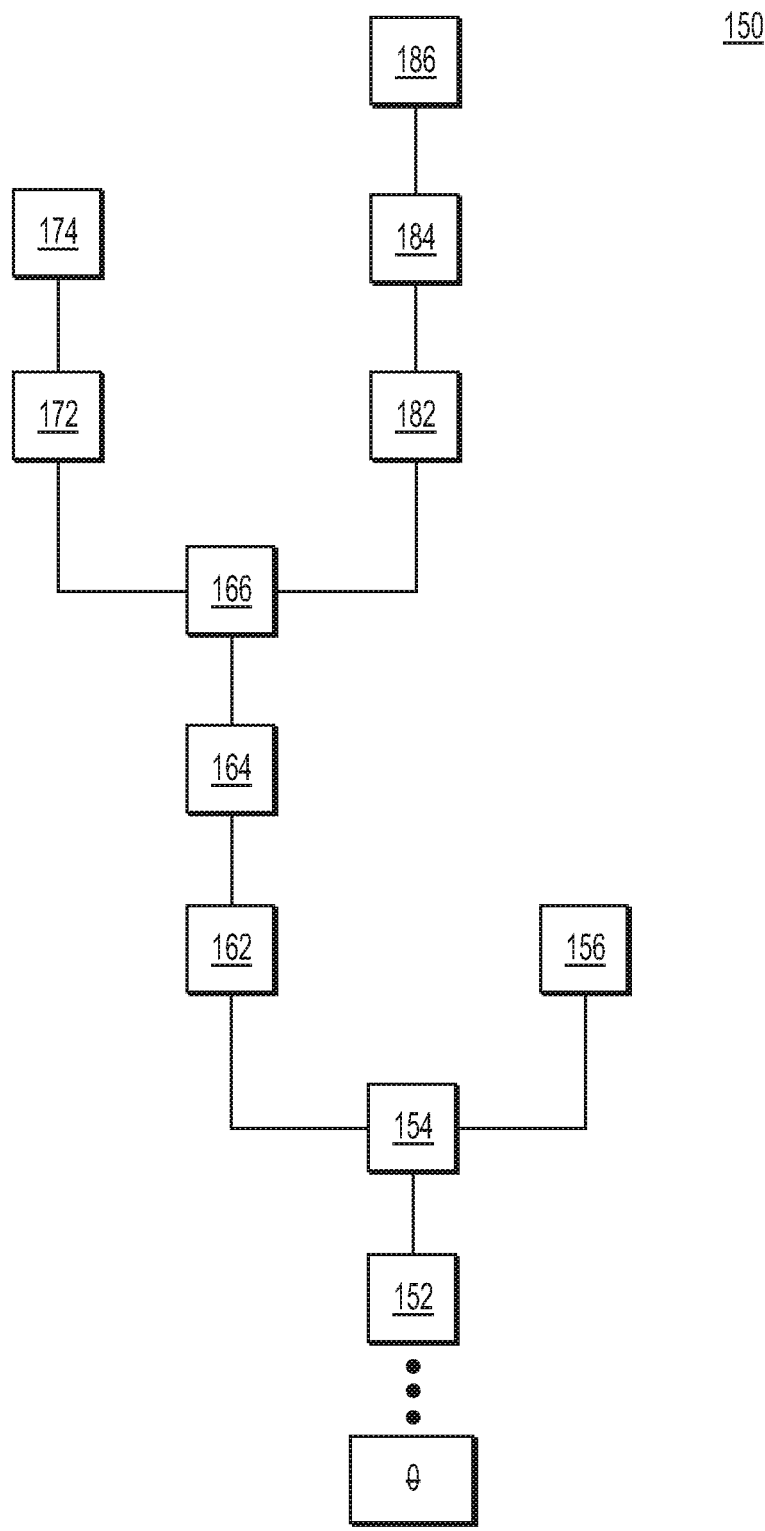
FIG. 1D illustrates an example blockchain (distributed/decentralized ledger) generated by the FREE system.

In some respects, the nodes 11-18 are equals (peers). For example, all nodes may include routing functions to participate in the network overlay 10, generate data and create transactions, propagate transactions and blocks, and discover and maintain connections to other nodes; and all nodes may maintain a complete copy of the blockchain 150 (FIG. 1D). All nodes also may autonomously verify any transaction without external reference. In an embodiment, all nodes participate in block verification. In another embodiment, certain nodes, designated as super nodes, perform block validation, and the remaining nodes "trust" this validation. One predecessor process to block validation may include transaction verification and aggregation, discussed in more detail herein. Finally, one or more nodes (e.g., node 18) may be a central authority for the network overlay 10. In this embodiment, node 18 may, among other functions, supervise block validation by the super nodes, may select and deselect super nodes, and may maintain whitelists and blacklists of devices that could try to access the blockchain.

In the example of node 19 joining the network overlay 10, one of the first substantial actions executed at node 19 is to construct (replicate) the entire blockchain 150 locally at a device of node 19. If the blockchain 150 is very long, this replication process could be time-consuming and bandwidth intensive. In an embodiment, node 19 may replicate the blockchain by downloading blocks from its neighboring nodes. The first node of the blockchain 150 may be statically embedded in programming issued by the central node 18 and thus is available at all conforming nodes. Node 19 may request and receive a version message from a neighboring node; the version message provides the height (HT) of the blockchain 150, which indicates how many blocks node 19 must download, and how many blocks a neighboring node may have (some nodes may not have a complete version of the blockchain 150). Through this process, node 19 may discover how many blocks to download, and from which node. Through an iterative process, node 19 replicates the full blockchain 150, requesting blocks from one or more nodes (doing so may reduce load on any one node to supply blocks, and may result in better bandwidth use). In a bandwidth-limited environment, or when link stability is marginal, a large blockchain download may not be practical, especially if conducted between node 19 and other "outlying" nodes, such as nodes 15-17. As an alternative, the central node 18 may provide a complete replication of the blockchain 150 to node 19. In another alternative, the node 19 may be instructed by the central node 18 to download only the last X numbers of blocks.

While FIG. 1B does not show components of the overlaid physical network 2, the computing devices of the nodes 11-18 communicate using hardware and software components of the network 2. FIG. 1C shows an example hardware structure, configured as a hybrid source/shared tree, of network 2 through which the nodes 11-18 communicate through a multicasting scheme in which any of the nodes 11-18 are configured to multicast. In FIG. 1C, network 2 is a wide area network, and source nodes 11 and 13 are multicasting records to other members (nodes) of the enterprise. The records travel from nodes 11 and 13 through routers A and C, which are components of network 2, to router B, which is installed as part of the computer device at node 14. Router B forwards both records to router D, which is a rendezvous point for the records, at node 18. Router D sends the records directly to node 15 and to router E, which is a component of network 2. Router E then sends both records to nodes 16 and 17. Note that at router D, the records are replicated and then forwarded to two different locations. Replication of a complete set of records (i.e., the entire blockchain 150) as an aspect of the FREE system 100 is discussed above. Thus, in multicasting records, components of the system 100 use the application layer of devices, such as routers and network switches, of the overlaid physical network 2 to execute multicasting operations.

As discussed herein, blockchain models implement a distributed database or a distributed (decentralized) ledger. However, decentralized ledgers may be implemented without blockchain technology. In an embodiment of the FREE system 100, blockchain technology is incorporated with a decentralized ledger. FIG. 1D illustrates example blockchain 150 (also see FIG. 2A). The blockchain 150 may be an open or a permissioned blockchain; FIGS. 1E(1)-1E(3) disclose aspects of permissioned embodiments of blockchain 150. In FIG. 1D, blockchain 150 is seen to include a main chain starting at genesis block 0 and proceeding to blocks 152 154, 162, 164, 166, 182, 184, and ending at block 186. Blocks in the main chain are the longest series of blocks that go from the beginning block 152 to the current block 186. For any block in the blockchain 150, only one path exists from block 152 to the current block 186. Blocks 156, 172 and 174 are not in the longest chain. Because the network overlay 10 is a distributed network, blocks 156, 172, and 174 may be generated only a few seconds apart from blocks in the main chain. Alternately, a fork in the main chain may occur (in certain embodiments of blockchain 150) when a user or member attempts to or succeeds in changing the content of a block. In some situations, when a fork occurs, the generating nodes build onto whichever block is received first in time. Alternately, the generating nodes may build onto blocks in either path in the blockchain. For the embodiment shown in FIG. 1D, the short chain of block 156 is not used after generation of block 164 and the short chain of blocks 172, and 174 is not used after generation of block 186.

The blockchain 150 (the distributed ledger) may include two record types, namely transactions and blocks. Transactions include the actual data (content) stored in blocks in the blockchain 150. In an aspect, the data in each transaction may be encrypted with its own unique key. Furthermore, blocks may include multiple transactions. Examples of the data include e-mail, images, audio recordings, and audio-text reports. The data examples may be generated at and by devices resident at or associated at the nodes in the network overlay 10. Transactions that include the data examples that are generated at nodes in the network overlay 10. As an aspect of the blockchain 150, the timing and sequencing of transactions in the blocks, and of the blocks themselves, may be recorded as part of a database containing the blockchain 150 or ledger.

In the network overlay 10, any node may generate a transaction. As part of the transaction generation, the generating node may sign the transaction to guarantee its authenticity. The node then multicasts the transaction, using the application layer of the physical network 2, through the network overlay 10, where each receiving node places the transaction in a temporary data structure. Certain nodes in the network overlay 10 may verify the transaction through a block validation process, and add the transaction to a block. Validated blocks then may be added to the blockchain 150. As additional blocks are added to the blockchain 150, previous blocks and their transactions are further confirmed. In an embodiment, all blocks and their transactions are, in time, made immutable. In another embodiment, the blocks may be edited; specifically, transactions incorporated into a block may be modified or deleted, as disclosed herein. In yet another embodiment, transactions waiting verification may be deleted, as disclosed herein.

Transactions may be digitally signed at the generating node using valid digital keys. In an embodiment, the FREE system 100 may use Identity Based Encryption (IBE), a public-key encryption algorithm based on each network overlay device (or member) having a unique identity (ID; e.g., an IP or e-mail address). A private key generator (PKG) distributes a master key and all private keys, which can then be used to create a unique public key for any ID. The public key is used to receive a transaction and the private key is used to sign the transaction. Transactions are encrypted using the locally created destination public key, and only the device (member) with the corresponding private key can decrypt the transaction.

FIGS. 1E(1) to 1E(3) illustrate aspects of blocks and transactions in the blockchain 150. FIG. 1E(1) illustrates embodiments of blocks and transactions used in the blockchain 150. In FIG. 1E(1), block 154 includes block header 154H and transactions 154$T_i$, where i=1-n, and block 162 includes block header 162H and transactions 162$T_j$. Transaction 154$T_1$ may include metadata, specifically a timestamp, a version, and a reference, and data. Some or all the metadata may form a transaction header. The data may be the content of the transaction. The transactions may be digitally signed. The data may be, for example, a video recording taken by devices at or associated with one of the nodes of network overlay 10. For example, node 11 of network overlay 10 may correspond to an unmanned airborne vehicle (UAV or UAS) that is employed in a wildfire suppression effort, the UAV capturing video imaging and relaying the video imaging to other entities involved in the firefighting effort. The timestamp may record the time the data are incorporated as a transaction, the version may indicate a set of rules the transaction follows, and the reference may record the position of the transaction 154$T_1$ in block 154. In an aspect, the decentralized ledger, in addition to storing the blockchain 150, also may store separately the transaction data and metadata for each transaction in block 154. The timestamp, reference, and data may be used to search for a specific transaction or data within the transaction. Finally, transaction 152T₁ may include code snippet (CODE) that may execute to delete the content of transaction 152T₁ upon the occurrence of certain conditions, such as a length of time from origin of the transaction 152T₁, thereby imposing a time-to-live limit on the existence of the transaction 152T₁ in the blockchain 150. Block 162 is similar in most respects to the structure to block 154.

The block header 154H includes a hash of the previous block header, 152H, Merkle Root 154T (see FIG. 1E(2)), version, time, and other information). Block header 162H includes a hash of block header 154H. Use of these chained hashes ensures there has been no tampering or alteration of the data in the blocks.

The data in transaction 154T₁ may be encrypted with a symmetrical key, a public-private key, or other cryptographic key. A common encryption key may be used for each transaction in block 154. For example, suppose that the user at node 14 wants to share a first video (transaction 154T₁) with nodes 15-18 and a second video (154T₂) with node 13. Only one decryption key would be required in this example since the identical encryption key was used for both videos (transactions). In another example, a unique key is used for each data item and the user at node 14 wants to share one video with nodes 15-18 and another video with node 13. Two keys would be independent and separate description keys would be needed in this example since two different encryption keys were used.

Optionally, the block header 154H also includes a file (not shown) with information that confirms when and in what sequence the transactions became journaled as part of the blockchain 150. The information in the file may or may not be encrypted. When a block contains multiple transactions T$_i$, the corresponding file may include the journaling information for each transaction T$_i$ of the block in the blockchain 150, since, typically, the journaling information would be the same for each such transaction T$_i$.

The FREE system 100 may incorporate a protocol to modify the content of blocks in the blockchain 150. The core of security of the blockchain 150 is the cryptographical linkage of all major components of the distributed ledger. Specifically:

Transactions are linked to each other mainly through a Merkle Tree (see the example of FIG. 1E(2));

The Merkle Tree has its root incorporated into the block header; and

The block header includes a reference to the preceding block header (see FIG. 1E(1)).

The cryptographically enforced interconnectivity fosters the stability and security of the blockchain 150. At any point, a break in the link between any of the records (blocks and transactions) may leave the blockchain 150 exposed to malicious attacks. In the blockchain 150, all data may be stored in transactions. Hence, in the context of the herein disclosed blockchain 150, transaction modification refers to the deletion of some or all data in a transaction T$_i$, or modification of data in the transaction T$_i$; ordinarily, this form of modification alters the Merkle root (produces a new Merkle root) in the block header, which could alter a hash of the block header, which could in turn, affect the security of the blockchain itself. To prevent this blockchain disruption, the FREE system 100 may include protocols that maintain the link (e.g., the Merkle root) between the transactions T$_i$ and the block header.

In one protocol embodiment, only certain elements of the transaction metadata (i.e., the transaction header) are hashed to form the Merkle root. The transaction's data may or may not be encrypted but in either event is not used to form the hash (i.e., the Merkle root). Thus, if the transaction's data are modified or deleted, that operation will not affect the link between the modified/deleted transaction and the block header. Thus, in this embodiment of the herein disclosed protocol, a request to delete/modify a transaction functions to maintain the original transaction header intact while deleting the transaction's data. In an aspect, following data modification/deletion, the protocol sets a flag ("this transaction was deliberately modified/deleted" (as the case may be)) indicating the data has been modified/deleted. Then, all conforming nodes will continue to verify the block and transaction, and will see the modification/deletion flag. The net result is that the blockchain remains secure and not interrupted. In another aspect, where the transaction data are stored separately (with node 18 only, for example, or with all nodes), the transaction data may be retained or deleted from the separate storage.

In another embodiment, the herein disclosed protocol replaces a transaction to be modified (e.g., deleted or modified data in the transaction) with a "special record" that includes all modified transaction information, the hash (Merkle root) of the transaction to be modified, that is being modified; and the special flag. Conforming blockchain nodes, recognizing the special flag, take the hash of the non-modified transaction when calculating the Merkle Tree hashes, thereby retaining the link of the block holding the modified transaction data with the rest of the blockchain. Additionally, conforming nodes are obliged to use the previous transaction information when looking up the transaction for verifying the outputs of the modified transaction. The special record at that stage of the protocol execution is not protected and may be freely modified. To secure the blockchain 150 from such an attack, the protocol uses a special type of transaction, namely a deletion/modification request transaction. Referring to FIG. 1E(3), a deletion/modification request transaction 155 includes a full copy of the new special record transaction 155A to replace the original transaction, the height (HT) 155B of the block where the original transaction resides, and the original hash 155C of the transaction. When this deletion/modification request is processed and validated, thereby producing a modified copy 157, which includes modified transaction 157A and the original hash 155C, all conforming nodes are obliged to replace the original transaction in the historical block HT with the special record found in the deletion/modification request 155, and accept the modified copy 157 as a valid (historical) transaction because of the presence of the confirmed and verified deletion/modification request transaction 155. Thus, the protocol provides the same security throughout the entire blockchain as before the modification with the exception that the modified transaction is secured only for blocks after the deletion/modification request. The data then may be deleted from storage of all the conforming nodes. The two protocols described above have the limitation that they can only be safely implemented on a permissioned blockchain with known processing nodes. A potential application in an open blockchain has two important security risks. First, because in an open blockchain there is no control over a node's behavior, a node might easily ignore deletion/modification request transactions without risk of any consequences. Second, a malicious party may continually issue deletion/modification request transactions thereby removing data stored on the blockchain and constantly rewriting the blockchain's history and weakening the blockchain's security. Any time-lag between the deletion/modification request transaction being processed and the actual deletion taking place, e.g., after many blocks, may provide a small safeguard against such an action. On permissioned blockchains (e.g., blockchain 150), the right to issue deletion/modification request transactions may be restricted only to certain trusted nodes (e.g., current super nodes). Additionally, on permissioned blockchains the good behavior of the nodes and control of the actual deletion of the data from the hard drives can be enforced by other means. Finally, the modified special record may include the reference of the deletion/modification request to ease the back-reference computation by eliminating the need for each node to create and maintain an index of such back-references (which transaction requested the modification of a modified transaction).

In an embodiment, the protocol may be implemented as a self-executing code snippet that exists alongside the data in each transaction of a block that is to be validated and that is executed to manage the process of deleting the transaction's data. Thus, the FREE system 100 includes a delete-record component that is embedded by the FREE system 100 in each record, and that functions to execute a deletion routine to delete the content of the record (transaction or block) when the record has not been validated by the requisite number of super nodes, or has not been validated within a set time limit by the super nodes. The delete-record code component (see CODE, FIG. 1E(1)) may include a rule set such as <delete record> if super node <3; <delete block> if validation time >t, and an executable that deletes the record's contents, including the code snippet. In an embodiment, all transactions may be subject to a time-to-live constraint. In another embodiment, only selected transactions are subjected to a time-to-live constraint. In an aspect of this embodiment, the originator of the transaction (the originating node) may choose to impose a time-to-live constraint. In another aspect, the central node 18, or other supervisory node may impose time-to-live constraints. In yet another aspect, the system 100 may incorporate a rule set that defines, and automatically imposes, time-to-live constrains. In yet another embodiment, the network overlay 10 operates without time-to-live constraints.

Because the FREE system 100 is based on a decentralized ledger, each of the nodes 11-18 may maintain a complete copy of the ledger (e.g., blockchain 150), adding records (e.g., blocks and their transactions) to the ledger as the records (blocks and transactions) are created and validated. However, each node may separately store transaction data and metadata and block metadata in a database having an easily searchable format (schema).

In an embodiment, the FREE system 100 may include, as disclosed herein, super nodes. In an aspect, at least three super nodes may be used. Depending on the degree of consensus selected for validating a block, some number between a majority of super nodes and all super nodes may be required to "vote" for a block for the block to be validated and added to the blockchain 150. Before the validation process, however, one or more of the super nodes may engage in block construction, or transaction aggregation—basically, assembling one or more transactions into a block that thereafter is subjected to a consensus validation process. In an embodiment, the super nodes may aggregate transactions using a relationship between and among the transactions. For example, in a scenario where transactions are email messages (or similar messaging) the relationship may be based on having a sender and one or more recipients. Thus, individual emails in a chain, and any attachments to individual emails, may be aggregated based on a sender/recipient protocol, as long as every email can trace back its origin to the original sender. The email chain and its attachments may be "placed" in a block, and the block may be validated and added to the blockchain 150. However, in some enterprise environments, and in some situations, such a message send/receive protocol may not be practical or useful. Thus, in addition to the message send/receive protocol, the FREE system super nodes may use transaction aggregation protocols based on other features and elements of the transactions. In an aspect, each super node in the network overlay 10 is provided a set of transaction aggregation protocols by which blocks may be created. Such blocks may have a temporal limit—once started, the block is considered generated and ready for validation after a set time such as one hour. A block also may have a size limit based on the number of bytes in the aggregated transactions. To prevent malicious attacks, the block limits and the aggregation protocols may be immutable. In one such aggregation protocol, transactions are given a priority rating, and the priority determines the position of each transaction in the block. One simple case bases priority on a timestamp associated with the transaction—the older the data in the transaction, up until a point, the higher the priority. However, aged transactions may have little value in some situations. Another transaction protocol bases priority on a number of factors, including the timestamp, the identity of the node for the given situation (a UAV videoing a wildfire may have a higher tactical/operational significance than a weather report), the identity of a recipient (if any—the transactions may be multicast), a classification of the transaction (the sender may provide an URGENT classification), keywords in a subject line (if provided—the enterprise may provide a set of keywords specific to a given situation; for example, and referring to FIG. 1F, the enterprise may provide quadrant Q (southeast) as a keyword, and any transactions emanating from quadrant Q or having the keyword "quadrant 0" in a subject line or body of a transaction may be given a highest priority). During the process of aggregating transactions, the super node may collect the transactions in a transaction pool, adding transactions to a queue as the transactions cross a priority threshold. A transaction's place in queue may change during the aggregation process. When a defined block limit is reached, the super node may close the block and distribute the block to other super nodes for validation. The super nodes may vote in a round robin fashion as part of the block validation process.

Since the FREE system 100 executes to generate network overlay 10, the underlying architecture of the overlaid network may affect (in a positive or negative manner) operations of the FREE system 100. For example, network 2 may employ multicast routers. Multicast-capable routers create distribution trees (see, for example, FIG. 1C) that control the path that IP multicast traffic takes through the network to deliver traffic to all receivers, and thus would control distribution of records among the nodes 11-18. The two basic types of multicast distribution trees are source trees and shared trees. The simplest form of a multicast distribution tree is a source tree with its root at the source and branches forming a spanning tree through the network to the receivers. Because this tree uses the shortest path through the network, it is also referred to as a shortest path tree (SPT). Unlike source trees that have their root at the source, shared trees use a common root placed at some chosen point in the network. This shared root is called a rendezvous point (RP). FIG. 1C shows a shared tree for the group consisting of nodes 11, and 13-18, with the root located at Router D. Shared trees are unidirectional. Source traffic is sent toward the RP on a source tree. The traffic then is forwarded down the shared tree from the RP (the RP may, but need not, be at a node in the shared tree, and hence a node in the network overlay 10) to reach all receiving nodes (unless a receiving node is located between the source and the RP, in which case the receiving node may be serviced directly). Both source trees and shared trees are loop-free. Records are replicated only where the trees branch. Since members (nodes) of multicast groups can join or leave at any time, the distribution trees may be dynamically updated. When all the active receivers on a particular branch stop requesting the traffic for a particular multicast group, the routers may prune that branch from the distribution tree and stop forwarding traffic down that branch. If one receiver on that branch becomes active and requests the multicast traffic, the router may dynamically modify the distribution tree and start forwarding traffic again. Source trees have the advantage of creating the optimal path between the source and the receivers. This advantage guarantees the minimum amount of network latency for forwarding multicast traffic. However, this optimization comes at a cost: the routers must maintain path information for each source. In a network that has thousands of sources and thousands of groups, this overhead can quickly become a resource issue on the routers. Shared trees have the advantage of requiring the minimum amount of state in each router. This advantage lowers the overall memory requirements for a network that only allows shared trees. The disadvantage of shared trees is that under certain circumstances the paths between the source and receivers might not be the optimal paths, which might introduce some latency in packet delivery. In multicast forwarding, the source is sending traffic to an arbitrary group of hosts that are represented by a multicast group address. The multicast router must determine which direction is the upstream direction (toward the source) and which one is the downstream direction (or directions). If there are multiple downstream paths, the router replicates the packet and forwards it down the appropriate downstream paths, which is not necessarily all paths. Which multicast tree configuration is used may depend on the size and complexity of the network, as well as its geological extent.

As explained herein, the FREE system 100 may connect to its members (nodes) in a multicast tree, established through the application layer of the physical network 2, that speeds the flow of records (blocks and transactions) in a bandwidth limited environment. That is, the network overlay 10 functions as a multi-cast tree. An aspect of the FREE system 100 includes mechanisms to build the multicast tree, and by extension, the network overlay 10. One approach for building the multicast tree is through use the greedy algorithm paradigm: When a node wants to become a member of a specific decentralized ledger, or network overlay, that node may use a FREE system lookup service to the find nodes that are close to it, based, for example, on a number of hops. Then the node may determine available bandwidth to each of its neighboring nodes. Finally, the node may select the neighboring node with the highest bandwidth. For example, in FIG. 1B, node 19 senses the network overlay 10 and then wants to join the network overlay 10 to download the decentralized ledger's records. The node 19 may have installed, or may concurrent with sensing the network overlay 10, install (download) components of the FREE system 10. Thereafter, the node 19 will determine it has two options: a 2 Mbps TTNT link 28 and a1 Mbps CDL link 29. The FREE system's QoS protocol will select the link with the higher bandwidth (link 28), reducing the time it takes for the node 19 to obtain the records. This example also illustrates an aspect of the FREE system's QoS capabilities, which are disclosed in more detail herein.

The addition of node 19 to the network overlay 10 illustrates another aspect of the FREE system 10, namely sensing the presence of, and then joining the network overlay 10. In an embodiment, node 19 queries domain name servers (DNSs) within range of node 19 to provide a list of IP addresses of current nodes in the blockchain 150.

In another embodiment, the FREE system 10 may include a lookup service accessible to nodes, such as node 14, that want to join the network overly 10. In an aspect, the FREE system 100 develops the lookup service. For example, node 14 bootstraps to the network 2 by conventional means, such as DNS or well-known IP addresses. Then the node 14 sends a discovery packet across the network 2, asking nodes that are within a certain distance to directly respond. The distance between nodes could be estimated using a route-trip time (RTT) probe. The RTT may be executed at the application level to overcome network firewalls.

In yet another embodiment, dedicated nodes (e.g., nodes 13 and 18) act as lookup service nodes. After node 14 bootstraps to the network 2, node 14 sends a packet to discover these lookup service nodes 13 and 18. Then node 14 can register its IP address with the lookup service nodes 13 and/or 18. Once registered with the lookup service nodes 13 and/or 18, the new node's IP address, or other address, may be sent (multicast) to some or all other nodes in the network overlay 10. The result of either registration process may be creation of a multicast group based on IP addresses, for example.

Alternately, once a node (e.g., node 14) has established a connection to the network overlay 10, the new node may send an addr message containing its own IP address to its neighboring nodes, which will, in turn forward the addr message to other nodes, thereby ensuring the newly added node becomes fully connected in the network overlay 10. In addition, the newly added node may send a getaddr message to its neighboring nodes asking those nodes to return an IP address list for other nodes in the network overlay 10.

During operation of the network overlay 10, nodes may come and go, and so each node in the network overlay 10 may execute an almost continual process of node discovery and connection (through use of the lookup service, or, alternately, using addr messaging) to ensure it maintains a viable link to at least one "active" node in the network overlay 10. Thus, the network overlay 10 dynamically adjusts without the need for a central membership control. See FIG. 1F.

In another aspect, to control admission to the network overlay 10, the FREE system 100 may provide discretionary blocking of access to and from blockchain 150. In an embodiment, the FREE system 100 recognizes three categories of user devices: restricted (blacklisted), allowed (whitelisted), and unknown. Restricted devices are those that are identified as belonging to users who are to be denied blockchain access (e.g., prisoners, criminals, terrorists). Restricted devices are not allowed access to the blockchain 150 and to the network overlay 10. Every user device has a unique identifying number or characteristic. In an embodiment, if the device identifying number or characteristic (e.g., subscriber number, IP address, MAC address) is configured to be "restricted," the FREE system 100 may accepts that device's access request and return a positive acknowledgement to the restricted device, which locks the restricted device to a component of the FREE system 10 (e.g., at node 18). This creates the illusion, at the user's device, that the user has gained access to and is operating within the network overlay 10, when, in fact, the device is locked to the FREE system 100 until the device is removed from the restricted access area (the extend of network overlay 10) imposed by the FREE system 100. By locking the "restricted" device to the FREE system 100, access by the device to the blockchain 150 is prevented while the "restricted" device is within the area of the network overlay 10. Allowed (whitelisted) devices are those configured in the FREE system 100 as to be allowed access. After determining the identity of the device, and determining that the device is an "allowed" device, the FREE system 100 directs the device to connect to the network overlay 10 by, for example, providing a node address for a conforming node. Once so directed, the allowed device's user can operate the device for normal transactions with the blockchain 150. Unknown devices are those not specifically recognized by the FREE system 100 as allowed (whitelisted) or restricted (blacklisted). Unknown devices may be allowed normal network overlay access depending, for example, on a security level requirement at a given location.

Figure 1F:
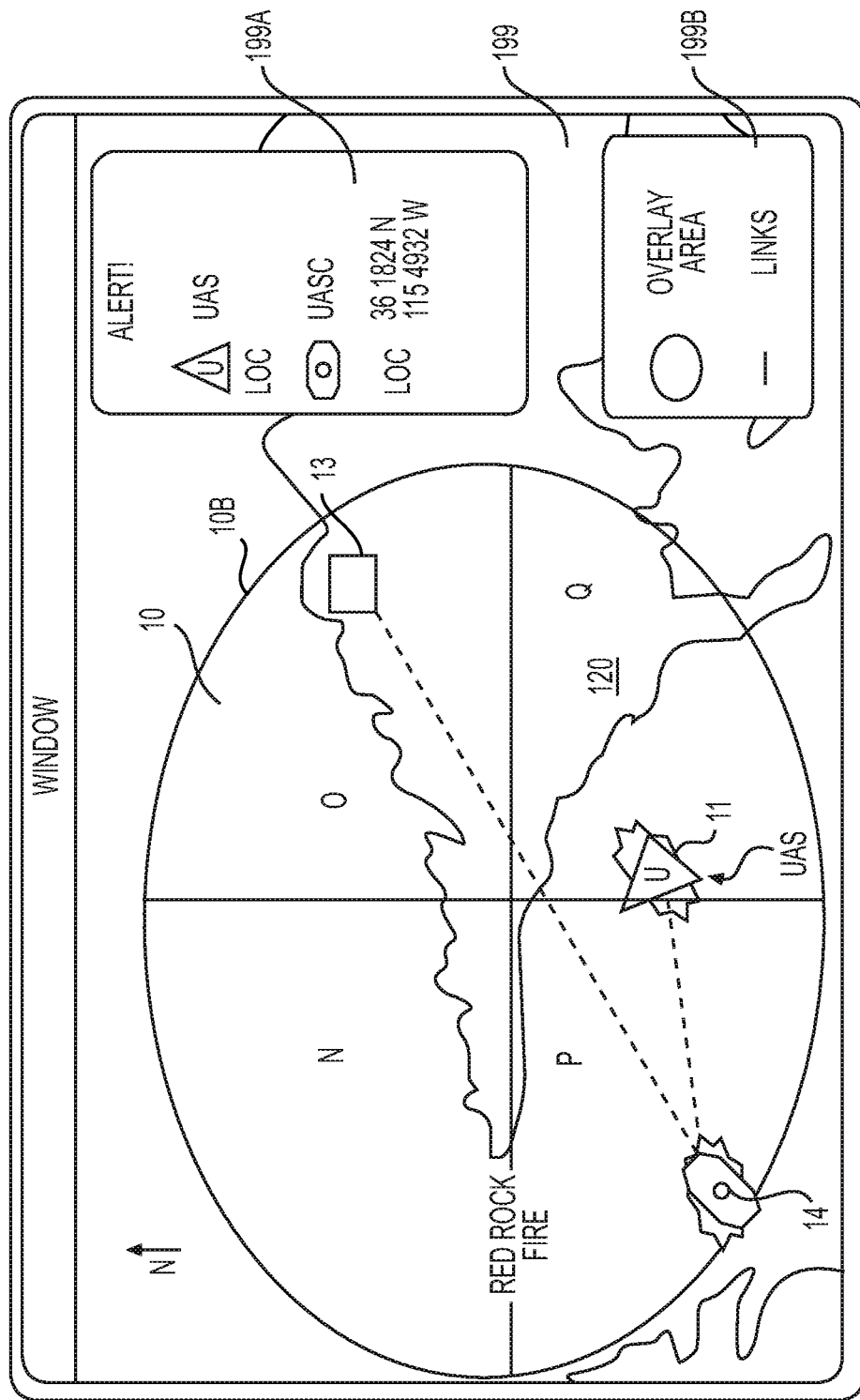
FIG. 1F illustrates an example graphical visualization of the network overlay of FIG. 1B.

As aspect of the lookup service, the FREE system 100 may provide a graphical visualization of the network overlay 10; FIG. 1F illustrates an example of such a graphical visualization 199. The visualization provides FREE system operators with a global view of the network overlay 10, enabling the operator to better monitor and manage the network overlay 10. For example, a system operator can override the protocol by adjusting the topology of the overlay network overlay 10 and by selecting more appropriate super nodes. The FREE system 100 may periodically, and automatically compute the available bandwidth between nodes using any available paths through the underlying physical network 2. Bandwidth sensing is performed at the application level to overcome network security policies (e.g., firewalls).

In FIG. 1F, display 199 includes data block 199A and legend block 199B. The display 199 shows network overlay boundary 10B surrounding nodes 11, 13, and 14 of network overlay 10. The nodes 11, 13, and 14 may communicate with each other using the network switches of the underlying physical network 2. As can be seen by the display, the network overlay 10 is established to communicate among enterprise elements combating the Red Rock wildfire. As the wildfire waxes and wanes, the boundary 10B may change, and new switches of the physical network 2 may come into use by the nodes 11, 13, and 14. The boundary 10B may adjust automatically to include sufficient switches of the physical network 2 so that the nodes 11, 13, and 14 are able to communicate effectively. To facilitate communications and data transfer among the nodes 11, 13, and 14, the network overlay 10 is shown divided into quadrants N-Q. The UAV associated with node 11 is seen to be flying in quadrant Q, and may be relaying data (still or video images) that allows wildfire control personnel at a local (mobile) control station (node 13) effectively fight the wildfire.

In the display 199, priority-based routing will be achieved at the application level. Each node 11, 13, and 14 may set up multiple queues for processing and routing incoming records. Also, the nodes may perform bandwidth throttling to prevent links from being overloaded. Each node may be aware of the available bandwidth to its neighbors. Thus, a node can control the rate at which the node sends transactions via each link to optimize the use of the physical network 2.

In some implementations, consensus algorithms for validating blocks and building blockchains may use very computationally intensive hash functions such as the SHA-256 algorithm to compute a metric known as proof-of-work (PoW). Such a process may be desired when the blockchain validation is executed by pseudo-anonymous entities, as in Bitcoin. For the blockchain 150, such a robust validation process may not be needed since all nodes in the network overlay 10, and in particular, the super nodes, are known and trusted. Further, processes such as PoW take a significant time to execute (up to ten minutes), which may not be acceptable in some environments, particularly where applications need to support real-time messages/transactions. Therefore, to increase block construction rates, the FREE system 100 may use a hybrid approach. In an embodiment of a first aspect of this hybrid approach, the FREE system 100 may use streaming algorithms executed by CPUs or ASICs to allow fast processing, especially if 8-bit character strings are not hashed by processing one character at a time, but by interpreting the string as an array of 32 bit or 64-bit integers and hashing/accumulating these wide word integer values by means of arithmetic operations (e.g. multiplication by a constant and bit-shifting). The remaining characters of the string which are smaller than the word length of the CPU may be handled differently (e.g. being processed one character at a time). In another embodiment, the process converts strings to a 32 or 64-bit numeric value and then applies a hash function. One aspect that avoids the problem of strings having great similarity is to use a cyclic redundancy check (CRC) of the string to compute a 32- or 64-bit value. While it is possible that two different strings will have the same CRC, the likelihood is very small and only requires that a check of the actual string be found to determine whether one has an exact match. In a second embodiment of this first aspect, the FREE system 100 may execute a practical byzantine fault tolerance algorithm (PBFT) to establish consensus in the blockchain 150. The PBFT algorithm may execute as follows: Each super node in the network overlay 10 maintains an internal state (ongoing specific information or status) of the blockchain 150. When a super node receives a block to validate, the super nodes uses information from the block in conjunction with their internal state to run a computation or operation. This computation in turn tells the super node whether the block is or is not valid. After reaching its individual decision about the block, the super node passes that decision to the other super nodes in the network overlay 10. A consensus decision is determined based on the total decisions provided by all super nodes. Second, the FREE system 100 may dynamically select dedicated nodes (super nodes) for achieving a distributed consensus that a block is valid and therefore may be added to the blockchain 150. Returning to FIG. 1B, nodes 13, 14, and 18 are designated as super nodes. The super nodes are trusted nodes with enough computational resources to build the blockchain. For example, the super nodes may incorporate ASICs that execute the specific aspects of the FREE system 100.

As disclosed herein, the super nodes 13, 14, and 18 will communicate among themselves using dedicated communications paths 33, 34, and 38 to achieve synchronization for transaction aggregations and block validation. The super nodes 13, 14, and 18 also communicate among themselves to provide fault tolerance for the overlay network 10 and the blockchain 150 during block validation processes. Finally, the super nodes 13, 14, and 18, as would any node in the network overlay 10, perform block verification before adding a new block to the local copy of the block chain 150.

In addition, the FREE system 100 may, through node 18, monitor the super nodes 13 and 14 for misbehaving (i.e., failures). If a node "misbehaves," the FREE system 100 may invalidate the misbehaving super node and select a new super node. The super nodes may exchange records and compute the same block. The super nodes then may vote to determine the correctness of each block. Since the super nodes execute the same hash algorithm, each node should (must) produce the same hash. Thus, to validate, each super node will verify the block, unless the super node "misbehaves." For example, a super node that does not produce the same hash as other nodes may be "misbehaving." Other forms of misbehavior may include an excessive time to compute the required hash. Once validated by the super nodes, a block may be released to other nodes on the network overlay 10.

FIG. 2A illustrates an example of the FREE system 100. The FREE system 100 includes program 200, which may be stored on non-transient, computer-readable storage medium 110, loaded into memory 120, and executed by processor 130. Aspects of the program 200 may be accessible through and may be displayed on a display of user interface 140. The program 200 may be implemented in part or in whole at one node, such as node 18 and in part at the remaining nodes 11-17. Certain nodes, for example nodes 13 and 14, may include additional aspects of the program 200 beyond that implemented at nodes 11, 12, and 15-17. In an embodiment, the program 200 may include aspects that are implemented in hardware or firmware. For example, certain nodes, such as 13 and 14 (and 18), may incorporate ASICs that allow execution of certain routines, such as the more computationally-intense routine of validating a block using a hybrid and consensus algorithm. Finally, the FREE system 100 includes database 149, which may store a shared, replicated, and decentralized ledger, an embodiment of which is blockchain 150. In addition, the database 149 may store data items and meta data 157 associated with the blockchain 150.

FIGS. 2B(1) and 2B(2) illustrate an example of program 200. Program 200 includes input/output (I/O) module 205, blockchain construction module 210, node discovery/look up service module 215, link sensing module 220, routing priority module 225, transaction edit module 230, encryption module 235, transaction verification module 240, block validation module 250, display generation module 260, and super node designation and monitoring module 270. The entire program 200 may be stored at node 18 while selected modules of the program 200 may be stored at other nodes in the network overlay 10. In addition, some modules, such as the validation module 250 may, for some nodes, be implemented as an ASIC. Following, each of the modules 205-270 are discussed in more detail. The discussion assumes the structure of physical network 2 and network overlay 10 (where all nodes of network overlay 10 are nodes of physical network 2).

The I/O module 205 provides nodes with the capability to communicate with other nodes in the network overlay 10.

The blockchain construction module 210 is executed to build and modify a decentralized ledger, such as the blockchain 150. The module 210 includes mechanisms to generate a static genesis block from which a blockchain is built, and mechanisms to add new blocks, and mechanisms to replicate blockchains.

The node discovery module 215 allows unknown nodes to register with and become members of the network overlay 10. The node discovery module 215 also allows known nodes to join or rejoin the network overlay 10. For example, new node 19 node may send a discovery packet across network 2, asking any node of network 2 that are within a certain distance of the new node to directly respond. Alternately, and possibly depending on the geographical extent of the network overlay 10, one or more nodes in the network overlay 10 may broadcast an attraction signal that prompts node 19 to send a discovery data packet. At one of the nodes, the module 215 may receive a data packet or other registration request from node 19. Once the data packet or registration request is received at any node in the network overlay, the receiving node may forward the data packet or registration request to the center node 18.

The link sensing module 220 is used to monitor available bandwidth on the links of the physical network 2 that are used for the actual transport of data among the nodes. Each node 11-18 in the network overlay 10 may test bandwidth on physical network links established or available to that node, and bandwidth sensing is performed at the application layer of network 2. The module 220 may include an algorithm that computes round trip time for an algorithm that takes as inputs measured data transmission times as disclosed above. Thus, each node may send small data packets over the link, compute the round-trip time, and use the computed time as a measure of bandwidth.

The routing priority module 225 includes a data intake queueing mechanism to handle incoming records, a bandwidth throttling mechanism to prevent overloading connected links, an QoS mechanisms that may, for example, recognize and process priority traffic from other nodes in the network overlay 10.

The transaction edit module 230 includes and provides a snippet of code and a rule set for each transaction of a record. The snippet executes to delete the content of the record under specified conditions reflected in the rules, such as failure to validate the record within a set time, or based on a user-defined timer.

The encryption module 235 provides one or more encryption algorithms that are used to create a hash of a record and to replicate a hash of a previous record. Each node may create a hash of a record and super nodes may replicate a hash of a previous record as part of the validation process that is a prerequisite for adding a record to the decentralized ledger. In an embodiment, the encryption algorithm is a streaming algorithm such as chacha20, for example.

The verification module 240 allows each node in the network overlay 10 to verify a block before the node adds the block to its local copy of the blockchain 150. The verification module 240 executes to compute a hash of the new block's header. The computed hash should match the hash of the highest block in the local copy of the blockchain 150. If the computed hash matches, the node adds the new block to the local copy of the blockchain 150.

The block validation module 250 may be distributed to super nodes in the network overlay 10. Alternately, the functions of the validation module 250 may be provided by an ASIC included in the computing system of each of the super nodes. In an aspect, nodes other than currently-designated super nodes may include the ASIC; however, the ASIC may be active only for currently-designated super nodes. Execution of the verification process of validation module 250 may occur much more rapidly with the ASIC as opposed to computations provided by a central processing unit (CPU), or processor. In either aspect, the module 250 will execute a consensus algorithm to verify the validity of each record before the record is added to the decentralized ledger. The consensus algorithm may require that each designated super node compute a hash of the record. The computed hash then is sent in a round-robin process to other super nodes, where the computed hashes are compared. Each such hash may have appended, the identity of the super node that computed the hash. In an embodiment, to validate a record, all computed hashes must match. In an example with three super nodes, a single node computing an incorrect hash will be easily identifiable.

The display generation module 260 generates a topological display 199 with the network overlay 10 displayed, including each node and a representation of the links between the nodes. An example is shown in FIG. 1D.

The supervisory module 270 may be implemented only at the central node 18. The supervisory module 270 includes mechanisms to select super nodes, including mechanisms to determine capabilities and capacities of processing and communications devices at each node in the network overlay. In addition, the supervisory module 270 includes mechanisms to monitor performance of the super nodes and other nodes in the network overlay. For example, the supervisory module 270 may record participation by super nodes in block validation, transaction aggregation, and transaction editing processes disclosed herein. The supervisory module 270 further includes mechanisms to select algorithms used in transaction and block verification, block validation, transaction editing, and multicasting processes disclosed herein.

Figure 3A:
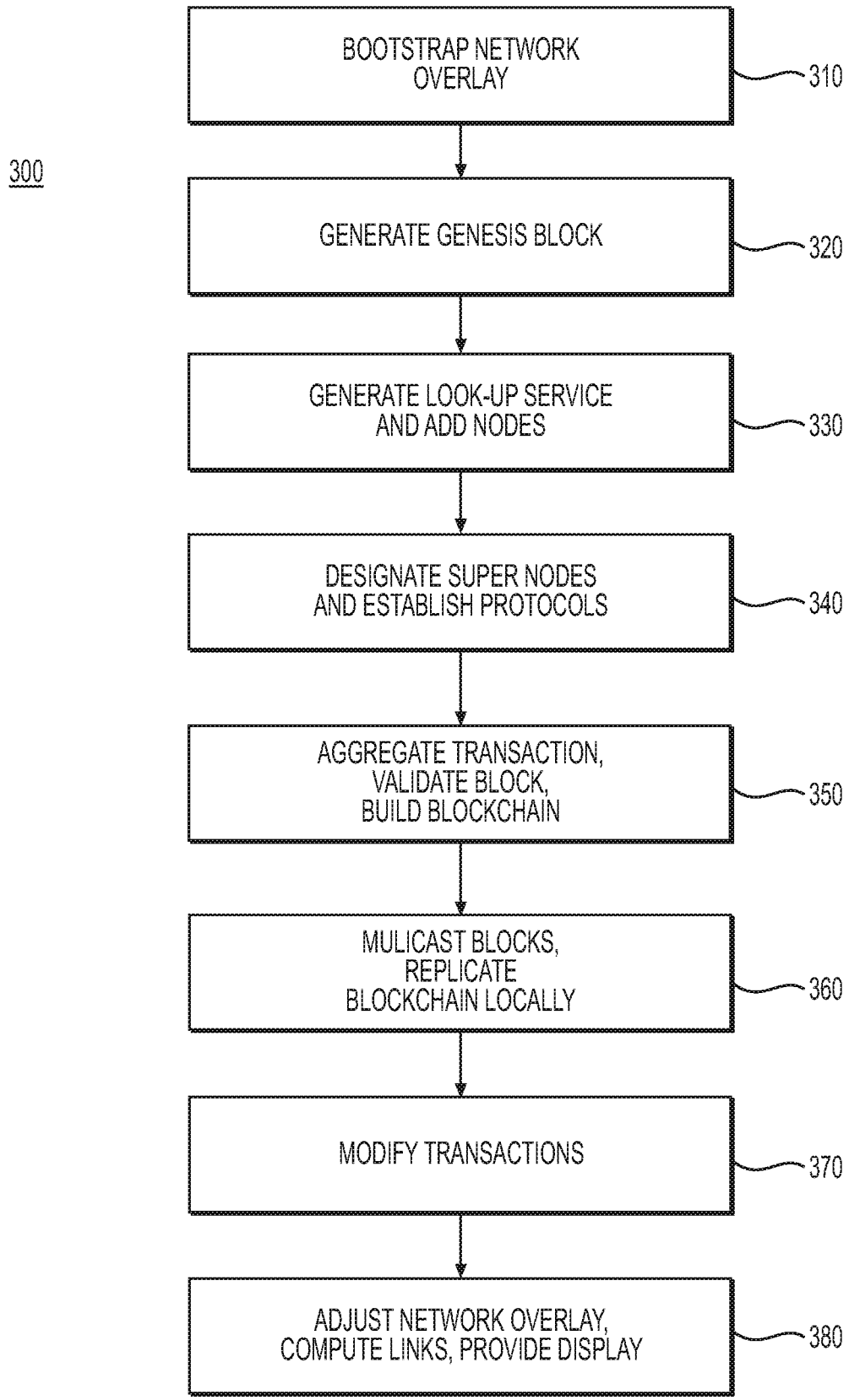

FIG. 3A illustrates an example process resulting from execution of FREE program 200 by processor 130. The steps (blocks) in the process are shown in a specific order; however, the steps of the process may be performed in different orders, some steps may be performed concurrently, some portions of some steps may be performed concurrently with portions of other steps, and additional steps may be included. The process is based on the disclosed FREE system 100, FREE program 200, and network overlay 10. In FIG. 3A, process 300 begins in block 310 when a node (e.g., node 8) on physical network 2 bootstraps network overlay 10 to establish a distributed ledger, which may be implemented as a permissioned blockchain. (In the network overlay 10, the physical node 8 is node 18 in the network overlay 10.) In block 320, the node 18 generates a genesis block (block 0) for the blockchain. In block 330, the node 18 generates a lookup service and accepts additional nodes into the network overlay 10. In block 340, the node 18 designates nodes in the network overlay 10 as super nodes, and establishes a transaction aggregation protocol and a block validation protocol. In block 350, nodes in the network overlay 10 generate transactions and the node 18 supervises the super nodes in a transaction aggregation process, a block validation process, and a blockchain construction process. In block 360, individual nodes replicate the blockchain locally. In block 370, one or more super nodes modify/delete transactions, thereby modifying corresponding blocks, and the modifications are replicated by all nodes in the network overlay 10. In block 380, the FREE program 200 executes to generate/adjust the network overlay 10, compute link parameters, and provide a display of the network overlay 10. Thus, the process 300 is a process for managing enterprise transactions using a distributed ledger and includes creating, by a processor, a network overlay to a physical communications network; adding one or more nodes to the network overlay; designating one or more nodes of the network overlay as super nodes; generating a distributed ledger to store the transactions; and replicating the distributed ledger to all nodes of the network overlay. Further, generating the distributed ledger includes receiving, at a super node, transactions from the one or more nodes, assigning, by the super node, the transactions to a variable size block, validating, by the super nodes, the variable size block, and linking the validated variable size block to the distributed ledger.

Figure 3B:
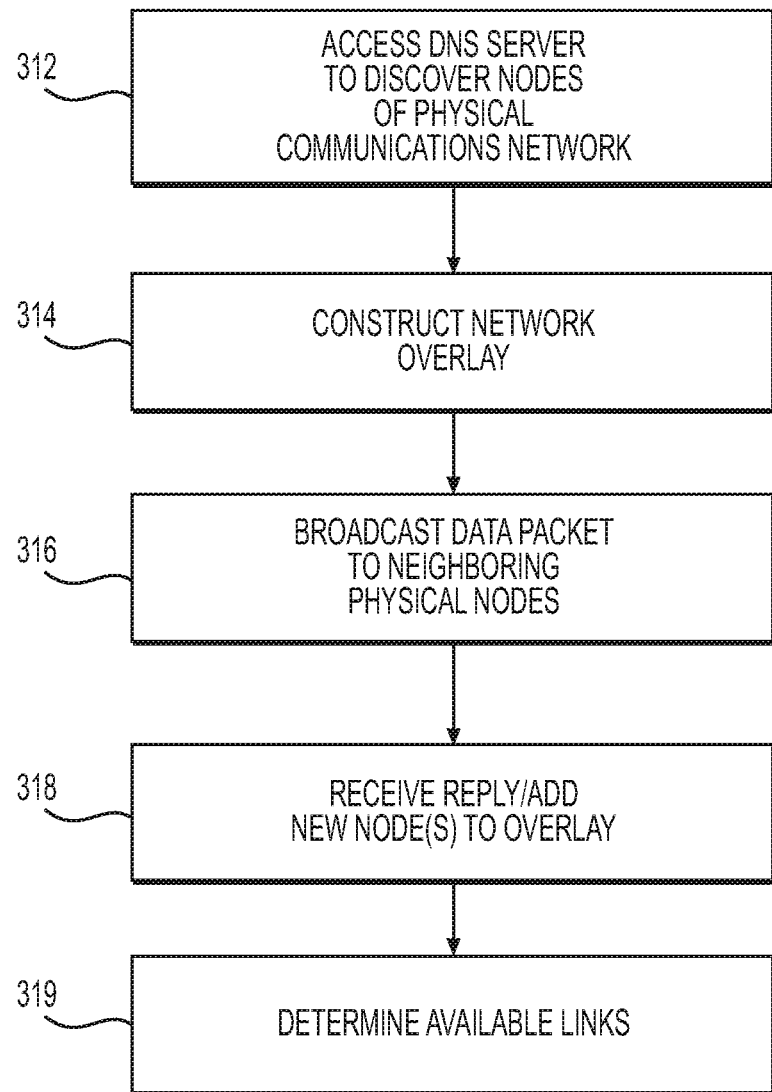

To create the network overlay 10, and subsequently generate a distributed ledger (i.e., blockchain 150) a node in an enterprise may perform bootstrap operation 310a, shown in FIG. 3B. Operation 310a begins in block 312 when a device at a node (e.g., a processor executing FREE program 200 at physical node 8 of physical network 2) accesses a DNS server, or other conventional devices and means, to determine a list of neighboring physical nodes associated with the enterprise, and that may be candidates to join a network overlay on the physical network 2 and to receive and build a distributed ledger. In block 314, a processor constructs network overlay 10 consisting at least of node 18 (corresponding to physical network node 8) and links to one or more additional nodes. Also in block 314, the device generates a list of neighboring physical nodes, including an identity, such as an IP or MAC address of each such node. In optional block 316, the device broadcasts a data packet, or join invite, to one or more of the neighboring physical nodes. In block 318, the device receives a join reply, and adds the replying physical node to the network overlay. In another embodiment, the device may access an existing list of neighboring physical nodes and may send a join invite to one or more nodes on the existing list. In block 319, the device at node 18 may determine available primary an alternate physical links to each node that joins the network overlay 10, as well as the bandwidth and round-trip time of each such physical link and the identity of any switches in the link. At the conclusion of operation 310a, the node 8/18 will have produced a network overlay 10 consisting of itself and one or more neighboring nodes. Thus, generating the network overlay (operation 310a) includes a processor identifying physical nodes in the physical communications network; assigning an overlay node to a physical node; and connecting the network overlay node to the physical node through an application layer of the physical communications network.

Figure 3C:
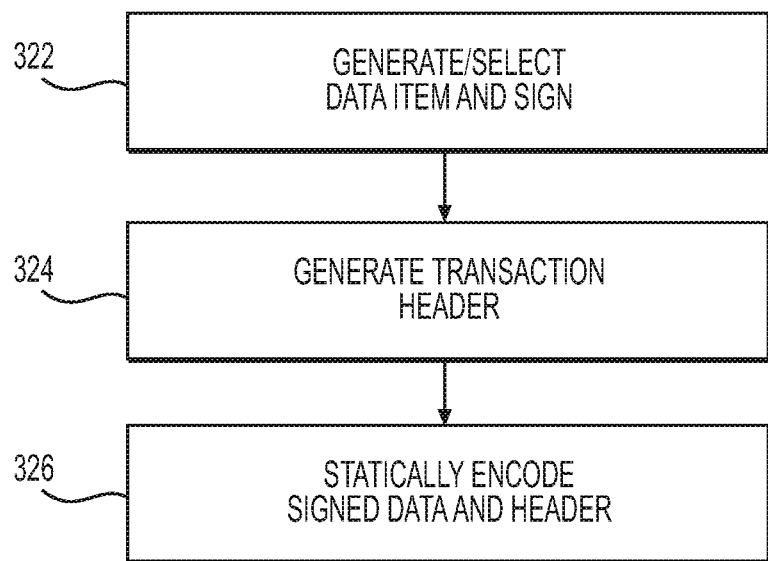

The enterprise implementing blockchain 150 may generate a genesis block, i.e., block 0 of blockchain 150. FIG. 3C illustrates example operation 320a for generating a genesis block. In block 322, the FREE program 200 executes to generate a first transaction (transaction 0) by first generating or selecting a data item, and digitally signing and encrypting the data item. Transaction 0 also will include a transaction header, which is generated in block 324, by generating a hash of the data item, assigning a timestamp, and providing other metadata. In block 326, Transaction 0 is statically encoded as block 0 within the blockchain 150, and thereafter is immutable. Block 0 then may be provided to each node of the network overlay 10 as a starting point for a locally-replicated version of blockchain 150.

Figure 3D:
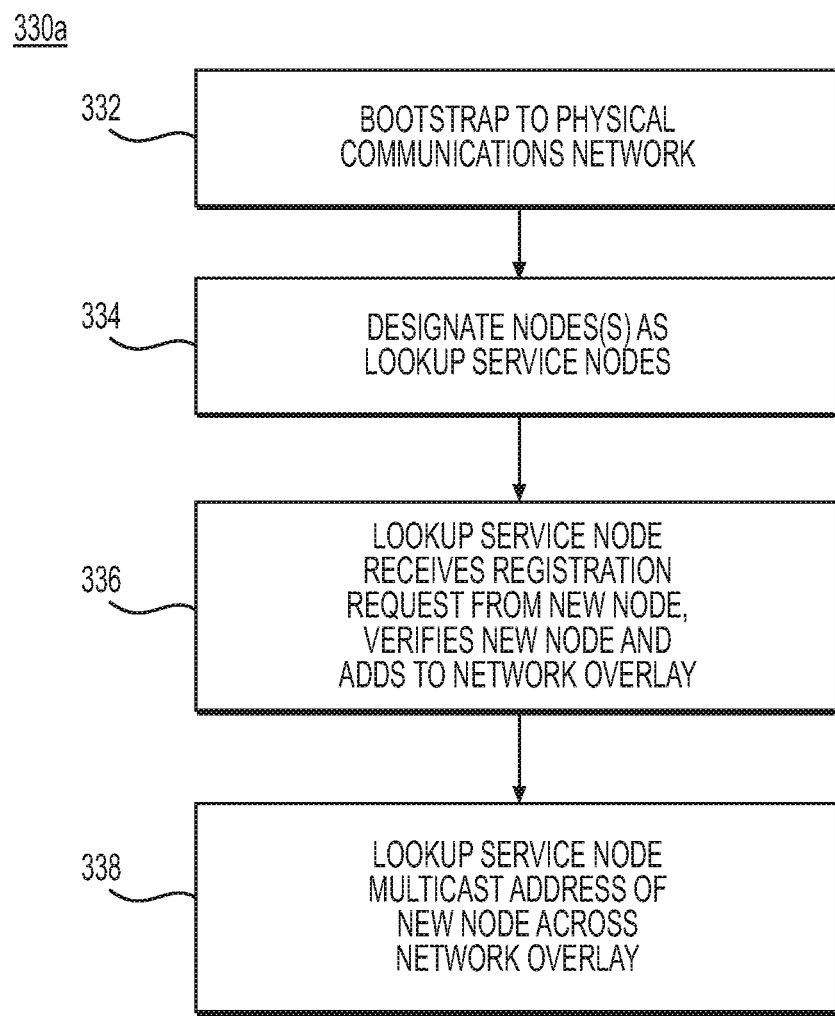

When a node wants to become a member of a specific decentralized ledger, or network overlay, that node may use a FREE system lookup service to the find nodes that are close to it, based, for example, on a number of hops. Then the node may determine available bandwidth to each of its neighboring nodes. Finally, the node may select the neighboring node with the highest bandwidth. For example, in FIG. 1B, node 19 senses the network overlay 10 and then wants to join the network overlay 10 to download the decentralized ledger's records. The node 19 may have installed, or may concurrent with sensing the network overlay 10, install (download) components of the FREE system 10. Thereafter, the node 19 will determine it has two options: a 2 Mbps TTNT link 28 and a1 Mbps CDL link 29. The FREE system's QoS protocol will select the link with the higher bandwidth (link 28), reducing the time it takes for the node 19 to obtain the records. This example also illustrates an aspect of the FREE system's QoS capabilities, which are disclosed in more detail herein. The addition of node 19 to the network overlay 10 illustrates another aspect of the FREE system 10, namely sensing the presence of, and then joining the network overlay 10. In an embodiment, node 19 queries domain name servers (DNSs) within range of node 19 to provide a list of IP addresses of current nodes in the blockchain 150. In another embodiment, the FREE system 10 may include a lookup service accessible to nodes, such as node 19, that want to join the network overly 10. FIG. 3D illustrates example operation 330a in which components of the FREE system 100 develop a lookup service and add nodes to the network overlay 10. In block 332, for example, a node bootstraps to the physical network 2 by conventional means, such as DNS or well-known IP addresses. At this point, the network overlay 10 may consist of node 13 and 18, and in block 324, the central node 18 designates node 13 as a lookup service node (in addition to node 18). In block 336, node 13 receives a registration request from node 14. Node 13 verifies node 14 is an approved/allowable node, sends node 14 an approval message, adds node 14 to the network overlay 10, and, in block 338, multicasts node 14's address across the network overlay 10. Finally, node 13 (and central node 18) store the node 14 address.

Figure 3E:
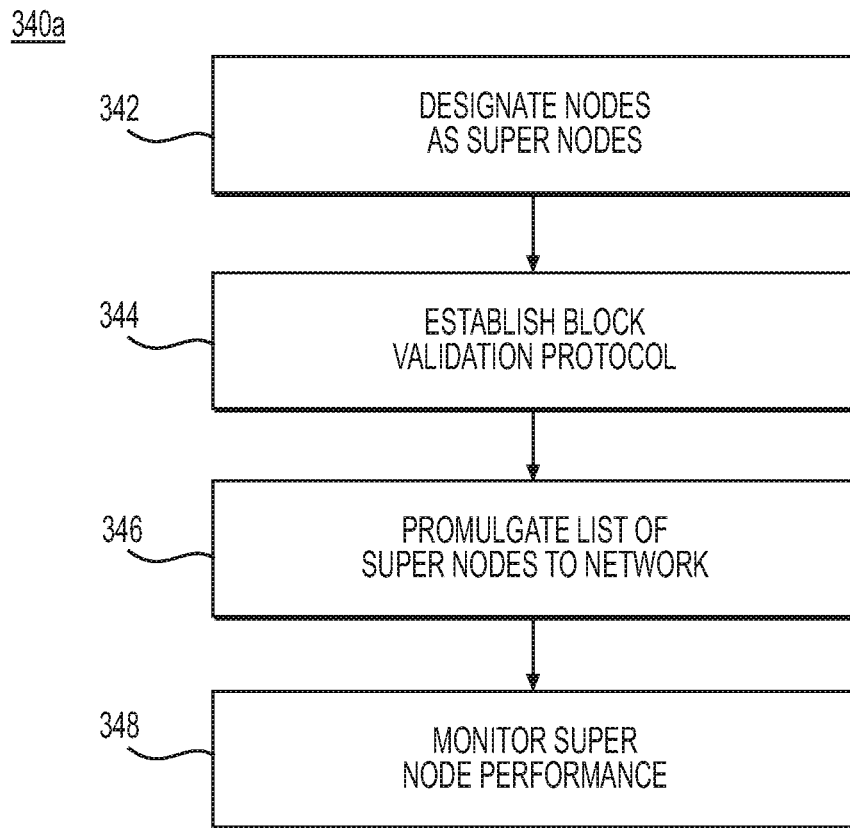

In block 340, the central node 18 executes process 340a to designate super nodes and establish protocols for transaction verification and block validation. Operation 340a, shown in FIG. 3E begins in block 342 when the central node 18 receives sufficient information from a sufficient number of nodes to designate a node sub group consisting of a specified number of super nodes. The super nodes may be trusted nodes and may have sufficient computing power to quickly, reliably, and securely aggregate transactions and validate blocks. In executing block 342, the central node 18 may consider the capabilities of devices associated with the nodes, the physical (geographical) location of the devices, link bandwidth and reliability between nodes of the super node group; any performance metrics associated with the devices and the nodes, the identity and experience of human users of the node devices, and other information, all of which may be provided to the central node 18 upon accretion of a node to the network overlay 10, and all of which may be evaluated by a ranking algorithm (not shown) executed at the central node 18. In block 344, the central node 18 may establish the basis for block validation, including the specific consensus algorithm to be executed by the super nodes. The consensus algorithm may include the required number of matching votes, from a quorum to complete consensus, and a specific hash function to use. The central node 18 may, but need not, designate itself as a super node. In block 346, the central node 18 may provide a list of the super nodes to all nodes in the network overlay 10. In block 348, the central node 18 may monitor operation of each super node, and may replace a faulty or misbehaving super node.

In an embodiment, the FREE system 100 may include, as disclosed herein, super nodes. In an aspect, at least three super nodes may be used. Depending on the degree of consensus selected for validating a block, some number between a majority of super nodes or all super nodes may be required to "vote" for a block for the block to be validated and added to the blockchain 150. Before the validation process, however, one or more of the super nodes may engage in block construction, or transaction aggregation—basically, assembling one or more transactions into a block that thereafter is subjected to a consensus process. The process 350a, shown in FIGS. 3F(1) and (2), begins in block 351, when a super node accesses one or more transactions and performs a transaction verification and aggregation process. An example aggregation and verification process is disclosed with respect to FIG. 4A. Returning to FIGS. 3F(1) and (2), the process of block 351 ends with a number of aggregated transactions that are contained within a new block to be validated. In block 352, the aggregating super node assigns the aggregated transactions to a new block. In an embodiment, all super nodes proceed with the transaction aggregation and verification process of block 351; the first super node to complete the process of block 351 assigns the aggregated transactions to the new block. In block 353, the aggregating super node multicasts the new block to the other super nodes in the overlay network 10. In block 354, each super node performs a validation operation to determine if the new block is valid and thus may be added to the blockchain 150. The validation operation of block 354 is disclosed in more detail with respect to FIG. 4B. In block 355, each super node provides its vote as to block validity to the other super nodes to determine individual matching scores. In block 356, the votes are tallied to determine if the block is valid. In an example of three super nodes, if two out of three matches result, the block is valid. In another example of three nodes, all three vote comparisons must result in a match for the block to be valid. In an aspect, the central node 18, which is one of the three super nodes, keeps track of the vote matching process. In block 356, if the new block is not valid, operation 350a moves to block 357, and the aggregating super node discards the block (the transactions, however, may be maintained in the transaction pool); if the block is valid, the operation 350a moves to block 358 and the super nodes add the block to their local copy of the blockchain 150. The operation 350a then moves to block 359, and the aggregating node multicasts the block to all nodes in the network overlay 10. In addition, in block 359, each super node may add metadata for the new block to a separate metadata file for the blockchain 150; the metadata may include a hash of the new block, a timestamp for the new block and the block height HT in the blockchain 150 for the new block.

Figure 3G:
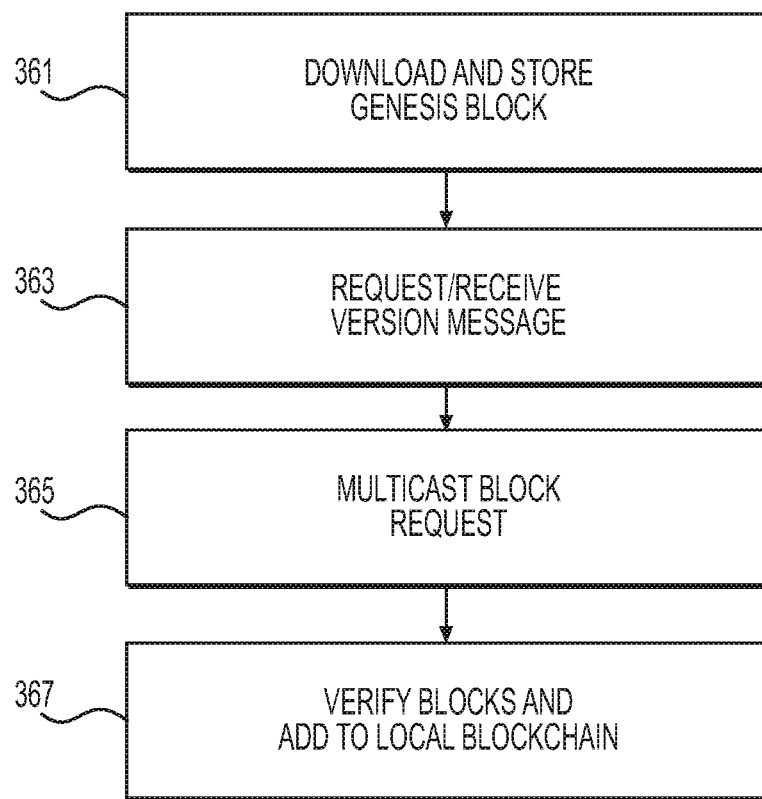
Figure 4A:
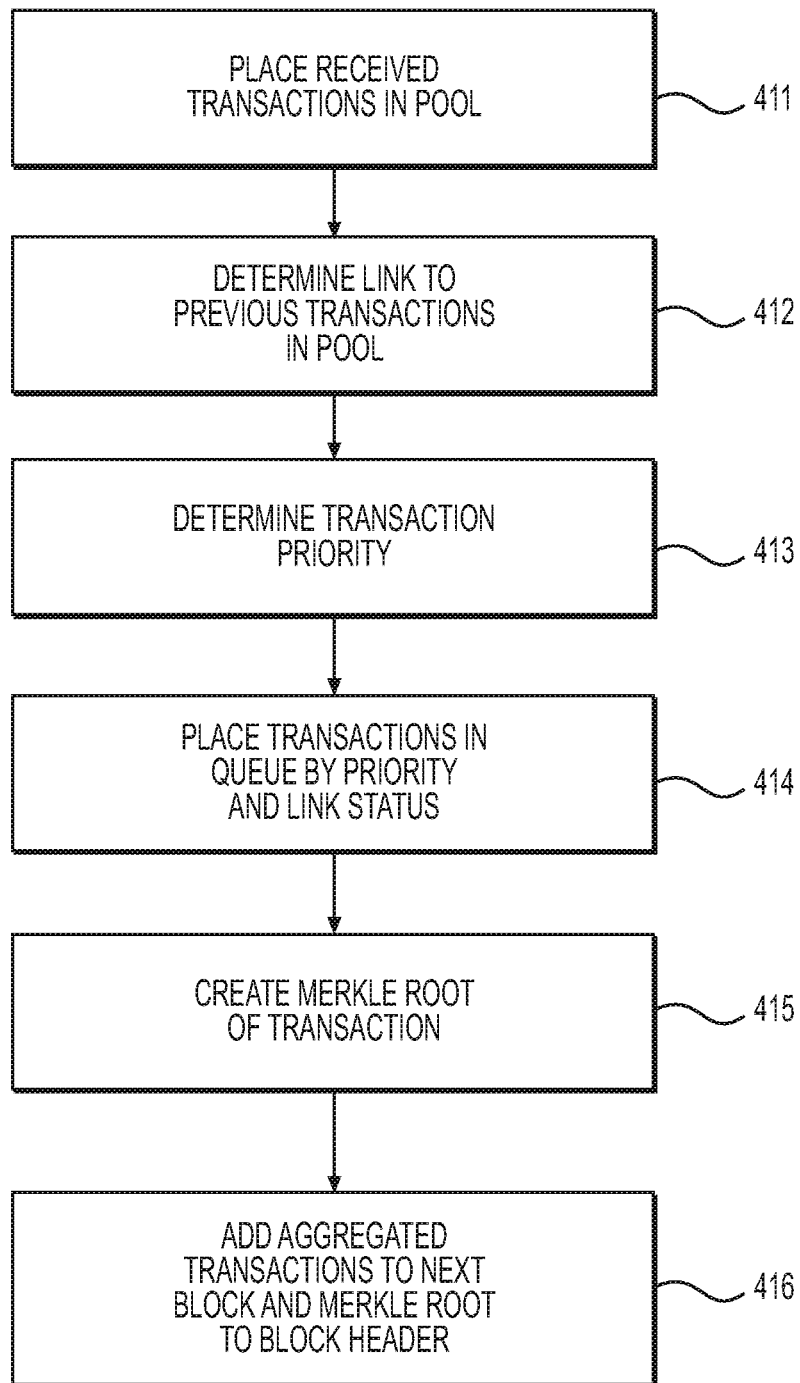
FIGS. 4A-4C illustrate additional example operations of the FREE system of FIGS. 2A-2B(2).
Figure 4B:
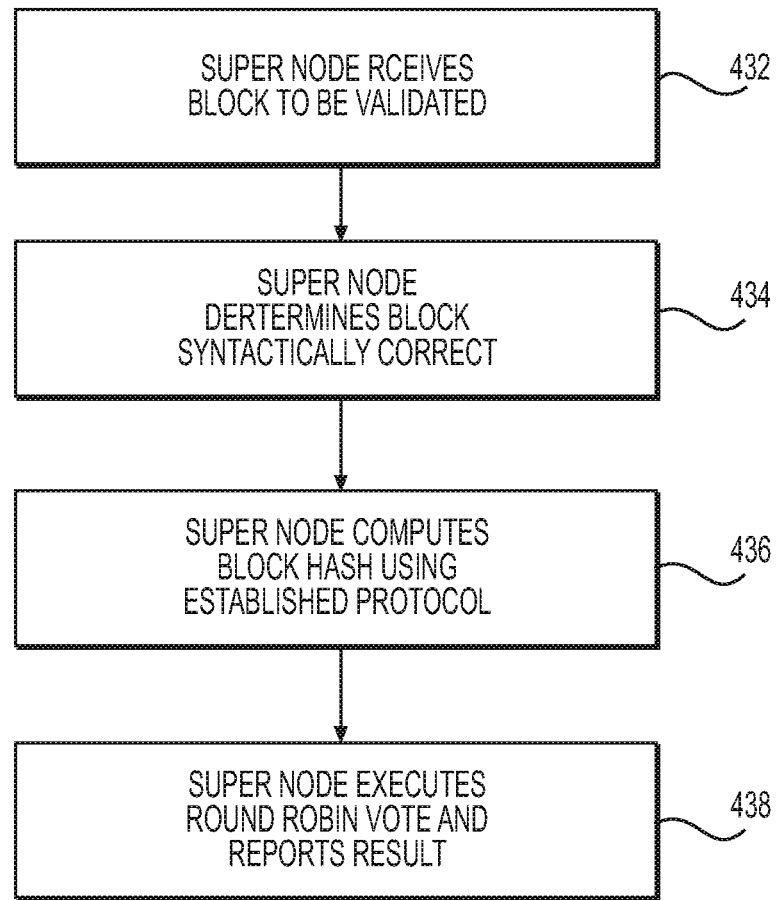
Figure 4C:
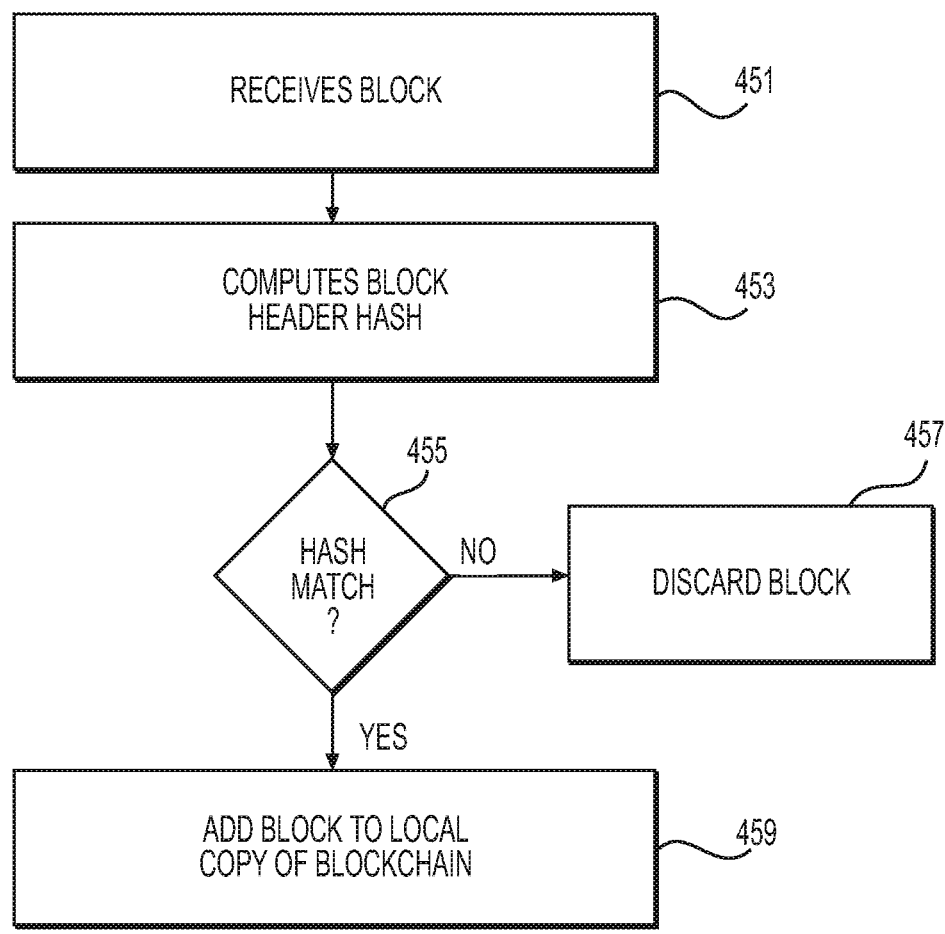

In the example of node 19 joining the network overlay 10, one of the first substantial actions executed at node 19 is shown in FIG. 3G as operation 360a, by which a device at node 19 executes FREE program 200 to construct (replicate) the entire blockchain 150 locally at the device of node 19. If the blockchain 150 is very long, this replication process could be time-consuming and bandwidth-intensive. Operation 360a begins in block 361 when the device at node 19 downloads and stores the genesis block for blockchain 150 (if not already stored at the device). In block 363, the device at node 19 may request and receive a version message from a neighboring node; the version message providing the height (HT) of the blockchain 150, which indicates how many blocks node 19 must download, and how many blocks a neighboring node may have (some nodes may not have a complete version of the blockchain 150). Through this process of block 363, node 19 may discover how many blocks to download and from which node. In block 365, node 19 requests one or more neighboring node to provide the blocks that node has that are not held by node 19. In block 367, node 19 adds the blocks received to its local version of blockchain 150 to produce a complete replication thereof. In adding a node to the blockchain (starting from block 0), the node 19 may execute a verification process, and embodiment of which is shown in FIG. 4C. Thus, through an iterative process, node 19 replicates the full blockchain 150, requesting blocks from one or more nodes (doing so may reduce load on any one node to supply blocks, and may result in better bandwidth use). In a bandwidth-limited environment, or when link stability is marginal, a large blockchain download may not be practical, especially if conducted between node 19 and other "outlying" nodes, such as nodes 15-17. As an alternative operation (not shown), the central node 18 may provide a complete replication of the blockchain 150 to node 19. In another alternative operation (not shown), node 19 may be instructed by the central node 18 to download only the last X numbers of blocks. In block 369, node 19 receives a new block, which may be multicast by a super node, and adds the new block to its local copy of the blockchain 150.

Figure 3H:
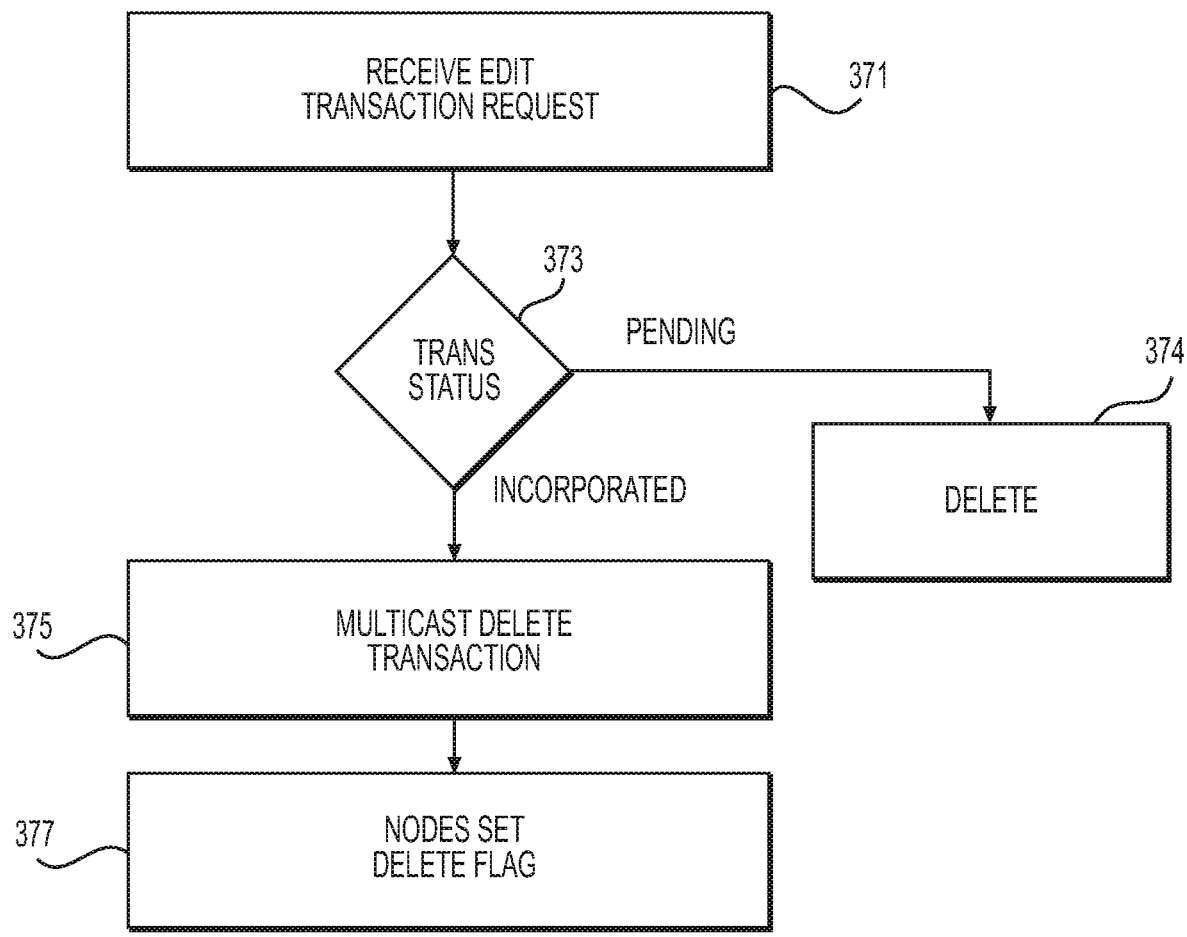

In an embodiment, the FREE program 200 may execute to edit (modify or delete) blocks and/or their transactions. In one aspect, a user/device/node may request a block or transaction be edited. In another aspect, the FREE program 200 may include a mechanism to automatically delete a transaction, either when the transaction has been incorporated into a block, or while the transaction is waiting block incorporation. FIG. 3H illustrates example operation 370a through which a transaction may be edited. Operation 370a begins in block 371 when a super node receives an edit transaction request from a node. In block 373, the super node determines if the transaction request pertains to an incorporated transaction or to a pending transaction. If the transaction is pending, the operation 370a moves to block 374 and the super node deletes the pending transaction, multicasts a delete message to each node, and the process 370a ends. If the transaction is incorporated, the operation 370a moves to block 375 and the super node issues a delete transaction, which is multicast to each node, and through which the transaction is deleted. In block 377, each node sets a flag ("this transaction was deliberately modified/deleted") indicating the data has been modified/deleted. Then, all conforming nodes will continue to validate the block and transaction, and will see the modification/deletion flag. The net result is that the blockchain remains secure and not interrupted. Thus, the operation 370a includes a super node receiving a transaction edit request from a node in the network overlay; determining the transaction is incorporated into a block of the distributed ledger; identifying a root hash of all transactions in the block incorporating the transaction in the transaction edit request; and editing the transaction in the transaction edit request without changing the root hash.

Figure 3I:
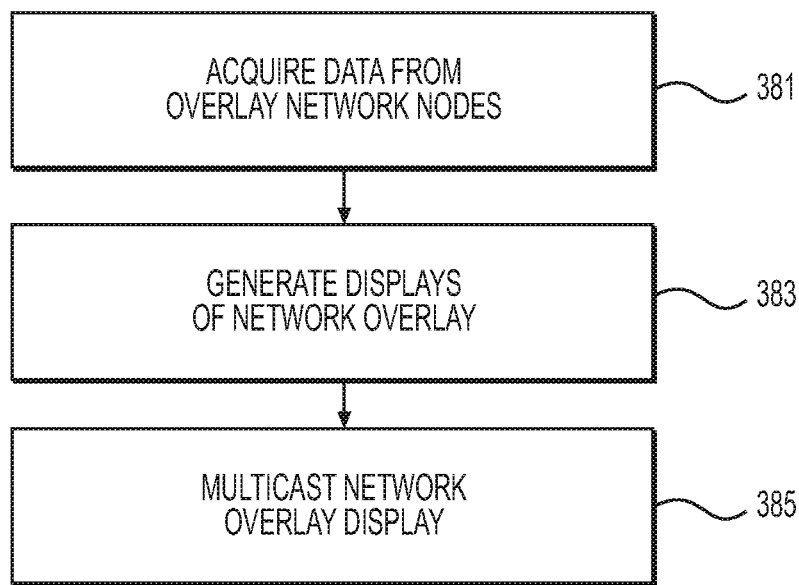

The FREE program 200 may provide a visual display of the network overlay 10. The display may include the topography over which the network overlay 10 is formed, as well as elements (switches, routers) of the underlying physical network 2. In addition, the display may include links between and among the nodes of the network overlay 10. FIG. 3I illustrates example operation 380a, in which the FREE program 200 generates and updates the display. In one aspect, the display at each node of the network overlay 10 may be centered on the that individual node. In another aspect, the display may have a common or reference center. The FREE program 200 may receive periodic updates from individual nodes. Each node may compute link bandwidth and round-trip time between it and its neighboring nodes using link sensor module 220 and may store the information locally, where the information is accessible by the FREE program 200 to generate the display. The operation 380a begins in block 381 where the FREE program 200 executes to access network data from the nodes in the network overlay 10. In block 383, the program 200 generates the display (e.g., the display 199 of FIG. 1F). In block 385, the program 200 provides (multicasts) the display to devices at each node of the network overlay 10. Thus, the display 199 includes an identification of one or more network overlay nodes, one or more physical nodes, and one or more links in the physical nodes; and the display 199 is adjusted as the network overlay changes. In one aspect, the display 199 may be generated at each node of the network overlay 10. In another aspect, the display 100 may be generated at a single node and then multicast to all or selected nodes of the network overlay 10. For example, the display 199 may not be sent to or generated by a UAV, but may be sent to a UAV control station.

In an embodiment, a super node may aggregate transactions using a relationship between and among the transactions. In an aspect, each super node in the network overlay 10 is provided a set of transaction aggregation protocols by which blocks may be created. Such blocks may have a temporal limit—once started, the block is considered generated and ready for validation after a set time such as one hour. Such blocks also may have a size limit based on the number of bytes in the aggregated transactions. To prevent malicious attacks, the block limits and the aggregation protocols may be immutable. In one such aggregation protocol, transactions are given a priority rating, and the priority determines the position of each transaction in the block. One simple case bases priority on a timestamp associated with the transaction. FIG. 4A illustrates transaction aggregation operation 410, performed by a super node. Operation 410 begins in block 411 when the super node receives a transaction (or generates a transaction) and places the transaction in a local transaction pool. In block 412, the super node determines if any link exists between transactions in the transaction pool. In block 413, the super node determines the transaction's priority. In block 414, the super node places the transactions from the transaction pool in queue based on priority and link status. In block 415, the super node computes an overall hash for the queued transactions (e.g., computes a Merkle root). In block 416, the super node adds the aggregated transactions to a (non-validated, new) block, and generates a block header.

In block 350 (FIG. 3A), when a defined block limit is reached, the aggregating super node may close the block and distribute the block to other super nodes for validation. FIG. 4B illustrates steps of an example block validation operation 430 that may be executed by each of the super nodes. Operation 430 begins in block 432 when a super node receives a block to be validated. In block 434, the super node determines that the structure of the new block (the block to be validated) is syntactically correct, the timestamp of the block is within some specified time in the future so that the block validation process may be completed; the block size is within a specified limit, and that the transactions in the block are valid. In block 436, the super node computes a hash of the block header to determine if the hash conforms to specific requirements, such as the hash must be less than some target value established by the central node 18. To compute the hash, in block 436, the super node may execute a specific hash algorithm such as a streaming hash algorithm or a practical byzantine fault tolerance algorithm (PBFT) to establish consensus in the blockchain 150. Alternately, in the example of the PBFT algorithm, the super node in the network overlay 10 maintains an internal state (ongoing specific information or status) of the blockchain 150. When a super node receives a block to validate, the super nodes uses information from the block in conjunction with their internal state to run a computation or operation. This computation in turn tells the super node whether the block is or is not valid. After reaching its individual decision about the block, in block 438, the super node passes that decision to the other super nodes in the network overlay 10.

After a super node multicasts a new, validated block, nodes in the network overlay execute operation 450 to verify the block and add the block to the node's local copy of the blockchain 150. In block 451, the node receives a new, validated block. In block 453, the node computes a hash of the block header. The hash should match the hash of the most current block in the blockchain 150. In block 455, the node determines if the hashes match. If the hashes do not match, the operation 450 moves to block 457, and the node discards the block. If the hashes match, the node adds the block to the node's local copy of the blockchain 150.

Certain of the devices shown in FIGS. 1A-2A include a computing system. The computing system includes a processor (CPU) and a system bus that couples various system components including a system memory such as read only memory (ROM) and random access memory (RAM), to the processor. Other system memory may be available for use as well. The computing system may include more than one processor or a group or cluster of computing system networked together to provide greater processing capability. The system bus may be any of several types of bus structures including a memory bus or memory controller, a peripheral bus, and a local bus using any of a variety of bus architectures. A basic input/output (BIOS) stored in the ROM or the like, may provide basic routines that help to transfer information between elements within the computing system, such as during start-up. The computing system further includes data stores, which maintain a database according to known database management systems. The data stores may be embodied in many forms, such as a hard disk drive, a magnetic disk drive, an optical disk drive, tape drive, or another type of computer readable media which can store data that are accessible by the processor, such as magnetic cassettes, flash memory cards, digital versatile disks, cartridges, random access memories (RAM) and, read only memory (ROM). The data stores may be connected to the system bus by a drive interface. The data stores provide nonvolatile storage of computer readable instructions, data structures, program modules and other data for the computing system.

To enable human (and in some instances, machine) user interaction, the computing system may include an input device, such as a microphone for speech and audio, a touch sensitive screen for gesture or graphical input, keyboard, mouse, motion input, and so forth. An output device can include one or more of a number of output mechanisms. In some instances, multimodal systems enable a user to provide multiple types of input to communicate with the computing system. A communications interface generally enables the computing device system to communicate with one or more other computing devices using various communication and network protocols.

The preceding disclosure refers to flowcharts and accompanying descriptions to illustrate the embodiments represented in FIGS. 3A-4C. The disclosed devices, components, and systems contemplate using or implementing any suitable technique for performing the steps illustrated. Thus, FIGS. 3A-4C are for illustration purposes only and the described or similar steps may be performed at any appropriate time, including concurrently, individually, or in combination. In addition, many of the steps in the flow chart may take place simultaneously and/or in different orders than as shown and described. Moreover, the disclosed systems may use processes and methods with additional, fewer, and/or different steps.

Embodiments disclosed herein can be implemented in digital electronic circuitry, or in computer software, firmware, or hardware, including the herein disclosed structures and their equivalents. Some embodiments can be implemented as one or more computer programs, i.e., one or more modules of computer program instructions, encoded on computer storage medium for execution by one or more processors. A computer storage medium can be, or can be included in, a computer-readable storage device, a computer-readable storage substrate, or a random or serial access memory. The computer storage medium can also be, or can be included in, one or more separate physical components or media such as multiple CDs, disks, or other storage devices. The computer readable storage medium does not include a transitory signal.

The herein disclosed methods can be implemented as operations performed by a processor on data stored on one or more computer-readable storage devices or received from other sources.

A computer program (also known as a program, module, engine, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The invention claimed is:

1. A computer-implemented method for managing enterprise transactions, comprising:
    creating, by a processor, a network overlay to a physical communications network;
    adding one or more nodes to the network overlay;
    designating a plurality nodes of the network overlay as super nodes, comprising:
        receiving an identification of a node and an identification of resource capabilities of a node, and
            determining the identified resource capabilities of the node are sufficient to allow the node to function as a super node, comprising, in a bandwidth-limited environment, using a link sensing mechanism to determine sufficient bandwidth is available at the node for transmission of information;
    generating a distributed ledger to store the transactions, comprising:
        receiving, at the super node, transactions from the one or more nodes,
        assigning, by the super node, the transactions to a variable size block,
        validating, by the super nodes, the variable size block, comprising each of a plurality of the super node executing a block validity voting process comprising:
        computing a hash based on the variable size block;
        comparing the hash to a target value;
        generating a block valid vote when the hash meets the target value and a block invalid vote when the hash does not meet the target value;
        accumulating block valid votes and block invalid votes from the super nodes; and designating the block valid when at least a majority of votes in the block validity voting process are block valid votes, and linking the validated variable size block to the distributed ledger; and replicating the distributed ledger to all nodes of the network overlay.

2. The method of claim 1, wherein generating the network overlay comprises:

identifying physical nodes in the physical communications network;

assigning a node in the network overlay to a physical node; and connecting the node in the network overlay to the physical node through an application layer of the physical communications network.

3. The method of claim 2, further comprising:

generating a display of the network overlay comprising an identification of one or more network overlay nodes, one or more physical nodes, and one or more links in the physical nodes; and adjusting the network overlay display as the network overlay changes.

4. The method of claim 1, wherein generating the distributed ledger further comprises:

generating a static genesis block as a first block of the distributed ledger;

generating a genesis block hash; and using the genesis hash to link the validated variable size block to the distributed ledger.

5. The method of claim 1, wherein assigning the transactions to the variable size block, comprises:

Identifying a priority value of each transaction and assigning each transaction based on the value of the transaction; and assigning transactions to the variable size block based on a remaining capacity of the variable size block and a time limit to complete the variable size block.

6. The method of claim 1, wherein replicating the distributed ledger, comprises:

a node receiving a current block height HT of the distributed ledger from one or more nodes in the network overlay;

the node determining blocks missing from the node's local copy of the distributed ledger to reach the current block height HT;

the node requesting and receiving a replica block of each missing block from one or more of the nodes in the network overlay; and the node verifying each received replica block and linking verified replica blocks to the local copy of the distributed ledger.

7. The method of claim 1, further comprising editing a transaction in the distributed ledger, comprising:

the super node receiving a transaction edit request from a node in the network overlay;

determining the transaction is incorporated into a block of the distributed ledger;

identifying a root hash of all transactions in the block incorporating the transaction in the transaction edit request; and editing the transaction in the transaction edit request without changing the root hash.

8. A non-transitory, computer-readable storage medium having encoded thereon a program comprising machine instructions implementing a distributed ledger to store and manage enterprise transactions, wherein one or more processors execute the machine instructions to:

create an overlay to a physical communications network, comprising the processors:

identifying physical nodes in the physical communications network, assigning an overlay node to a physical node, and connecting the overlay node to the physical node through an application layer of the physical communications network;

designate a plurality of overlay nodes of the overlay as super nodes, wherein the processors:

receive an identification of a node and an identification of resource capabilities of the node, and determine the identified resource capabilities of the node are sufficient to allow the node to function as a super node, comprising, in a bandwidth-limited environment, using a link sensing mechanism to determine sufficient bandwidth is available at the node for transmission of information;

receive, at physical nodes corresponding to the super nodes, transactions from physical nodes corresponding to the one or more overlay nodes;

assign, through the super nodes, the transactions to a variable size block;

validate, through the super nodes, the variable size block, comprising the processors at a plurality of the super nodes, execute a block validity voting process in which the processors:

compute a hash based on the variable size block;

compare the hash to a target value;

generate a block valid vote when the hash meets the target value and a block invalid vote when the hash does not meet the target value;

accumulate block valid votes and block invalid votes from the super nodes; and designate the block valid when at least a majority of votes in the block validity voting process are block valid votes, link the validated variable size block to the distributed ledger; and replicate the distributed ledger at all overlay nodes of the overlay.

9. The non-transitory, computer-readable storage medium of claim 8, wherein a processor generates the distributed ledger, comprising the processor:

generating a static genesis block as a first block of the distributed ledger;

generating a genesis block hash; and using the genesis hash to link the validated variable size block to the distributed ledger.

10. The non-transitory, computer-readable storage medium of claim 8, wherein when assigning the transactions to the block the processors execute the machine instructions to:

identify a priority value of each transaction and assigning each transaction based on the value of the transaction; and assign transactions to the variable size block based on a remaining capacity of the variable size block and a time limit to complete the variable size block.

11. The non-transitory, computer-readable storage medium of claim 8, wherein replicating the distributed ledger, the processor executes the machine instructions to:

receive a current block height HT of the distributed ledger from one or more nodes in the network overlay;

determine blocks missing from a node's local copy of the distributed ledger to reach the current block height HT;

request and receive a replica block of each missing block from one or more of the nodes in the network overlay; and verify each received replica block and link verified replica blocks to the local copy of the distributed ledger.

12. The non-transitory, computer-readable storage medium of claim 8, wherein the processors execute the machine instructions to edit a transaction in the distributed ledger, comprising a super node processor:

receiving a transaction edit request from a node in the network overlay;

determining the transaction is incorporated into a block of the distributed ledger;

identifying a root hash of all transactions in the block incorporating the transaction in the transaction edit request; and editing the transaction in the transaction edit request without changing the root hash.

13. The non-transitory, computer-readable storage medium of claim 8, wherein the processors execute the machine instructions to:

generate a display of the network overlay comprising an identification of one or more network overlay nodes, one or more physical nodes, and one or more links in the physical nodes: and adjust the network overlay display as the network overlay changes.

14. A computer-implemented method for storing and managing enterprise data using a distributed ledger, comprising:

receiving by a processor, transactions from nodes in a communications network;

through an application layer of the communications network, aggregating one or more of the transactions in a block, comprising:

verifying each of the one or more transactions, creating a hash of the one or more transactions, and adding the one or more transactions to a block and adding the hash to a header of the block;

through the application layer, validating the block, comprising:

designating one or more of the nodes in the communications network as trusted nodes, comprising determining a node has sufficient computing resources for validating the block, comprising, in a bandwidth-limited environment, using a link sensing mechanism to determine sufficient bandwidth is available at a node for transmission of information, executing a consensus algorithm by at least a majority of the trusted nodes in the communications network, and generating a hash of the block; comprising:

generating a hash of the block, comparing the hash to a target value, generating a block valid vote when the hash meets the target value and a block invalid vote when the hash does not meet the target value, accumulating block valid votes and block invalid votes from the trusted nodes, and designate the block valid when at least a majority of votes are block valid votes;

linking the block to a predecessor block in the distributed ledger, comprising verifying the hash of the block is lower than a hash of a top block in the distributed ledger; and replicating the distributed ledger across the communications network, comprising multicasting the block to each node in the communications network.

15. The method of claim 14, further comprising editing the distributed ledger, comprising:

a trusted node receiving a transaction edit request from a node in the network overlay;

determining the transaction is incorporated into a block of the distributed ledger;

identifying a root hash of all transactions in the block incorporating the transaction in the transaction edit request; and editing the transaction in the transaction edit request without changing the root hash.

16. The method of claim 14, wherein replicating the distributed ledger further comprises:

a node receiving a current block height HT of the distributed ledger from one or more nodes in the network overlay;

the node determining blocks missing from the node's local copy of the distributed ledger to reach the current block height HT;

the node requesting and receiving a replica block of each missing block from one or more of the nodes in the network overlay; and the node verifying each received replica block and linking verified replica blocks to the local copy of the distributed ledger.

* * * * *